US012129482B2

(12) United States Patent
Kendall et al.

(10) Patent No.: US 12,129,482 B2
(45) Date of Patent: Oct. 29, 2024

(54) METHODS FOR GENERATING, EVALUATING, GENE EDITING AND CLONING PLURIPOTENT STEM CELLS COMPRISING A LETHAL HAPLOTYPE

(71) Applicant: Inguran, LLC, Navasota, TX (US)

(72) Inventors: David Kendall, Beloit, WI (US); Diego Moreno, Navasota, TX (US)

(73) Assignee: INGURAN, LLC, Navasota, TX (US)

( * ) Notice: Subject to any disclaimer, the term of this patent is extended or adjusted under 35 U.S.C. 154(b) by 223 days.

(21) Appl. No.: 17/383,279

(22) Filed: Jul. 22, 2021

(65) Prior Publication Data

US 2022/0025323 A1 Jan. 27, 2022

Related U.S. Application Data

(60) Provisional application No. 63/056,386, filed on Jul. 24, 2020.

(51) Int. Cl.
*C12N 5/0735* (2010.01)

(52) U.S. Cl.
CPC ...... *C12N 5/0606* (2013.01); *C12N 2501/115* (2013.01); *C12N 2501/415* (2013.01); *C12N 2501/727* (2013.01); *C12N 2502/13* (2013.01)

(58) Field of Classification Search
CPC ............ C12N 5/0606; C12N 2501/115; C12N 2501/415; C12N 2501/727; C12N 2502/13; C12N 2502/1323; C12N 5/0604; C12N 5/0603; G01N 33/5005
See application file for complete search history.

(56) References Cited

FOREIGN PATENT DOCUMENTS

| WO | 2019100018 A1 | 5/2019 |
| WO | 2019140260 A1 | 7/2019 |

OTHER PUBLICATIONS

Schwenger et al, "Detection of the homozygous recessive genotype for deficiency of uridinfe monophosphate synthase by DNA typing among bovine embryos produced in vitro", Journal of Reproduction and Fertility (1994) 100, 511-514. (Year: 1994).*
International Search Report and Written Opinion issued on Dec. 21, 2021 in related PCT Appl. No. PCT/US21/42790.
Wakayama et al., "Mice cloned from embryonic stem cells" Proc Natl Acad Sci USA, Dec. 21, 1999; 96(26):14984-14989.
Wu et al. "An alternative pluripotent state confers interspecies chimaeric competency" Nature, May 21, 2015; 521(7552): 316-321.
Ludwig et al. Feeder-independent culture of human embryonic stem cells Nature Methods, vol. 3, No. 8, Aug. 2006, pp. 637-646.

(Continued)

*Primary Examiner* — Jeremy C Flinders
*Assistant Examiner* — Thomas R. Amick
(74) *Attorney, Agent, or Firm* — Ryan Christensen; Hashim Rahman

(57) ABSTRACT

The invention includes a method of evaluating a bovine embryo by fertilizing an egg obtained from a first bovine heterozygote of a recessive lethal haplotype with sperm cells obtained from a second bovine heterozygote of the recessive lethal haplotype; producing the embryo from the fertilized egg, wherein the embryo is homozygous for the lethal haplotype; establishing a cell culture from the embryo; collecting a plurality of cultured cells; and obtaining omics data, comprising one or more features, from the plurality of cultured cells.

12 Claims, 9 Drawing Sheets

Specification includes a Sequence Listing.

| | Haplotype | Hap Annotation | Seq |
|---|---|---|---|
| SEQ ID NO 1 | HH2 | Unknown causal | AAATTTTCAAAGGTAAGAAAAGTGGGGAGTTTGTG[A/G]CTGCATGATACCAAATGAATACTGCAGGCATTTTA |
| SEQ ID NO 2 | JH1 | Causal | TTAGACAGACCACTCAGGATGCCCCTGAAGAGGTT[C/T]GAAACCGTGACTTCAGGAGAGAGTTGGAGGAGAGA |
| SEQ ID NO 3 | HH2 | Unknown causal | ATTCTAAATCACTGGACCACCAGGGAACTCCTTAT[C/T]CAACACTTTCTTGTAATAAAATGTTAGATAGTG |
| SEQ ID NO 4 | JH1 | Flanking | TCATTAGAGGGCTGTATCAATAATCCTCATATCCT[A/G]TTCCGAGATTCTTGCATGCTAGGAGTTGAATTTGA |
| SEQ ID NO 5 | HH2 | Unknown causal | CCCCAACAATCATGAGCTTCCCATCTCAATGTGAC[A/G]TCAGTGAAGGCCACATGAGGAGTAGTGATGAGGTA |
| SEQ ID NO 6 | BH1 | Unknown causal | TTCTAAGTATATGCTGGCCATTGTCCTCTTGATAA[A/G]AGGTGTCACTCATGTTGTGGTGACCAAAGCCTGCA |
| SEQ ID NO 7 | HH3 | Flanking | CACAGTTCTGTGCACCCAGGTGTCAACAACTCCAT[A/C]ACACTCGGCCTAAAGCATCGCTTTGCTGGTGTCTG |
| SEQ ID NO 8 | HH2 | Unknown causal | GTCTATTCCTGGAACTTTCCCCACTTCAGGGAACC[C/T]AGGAGCAGGATAGCAAACCCACCCAATCATTCCAC |
| SEQ ID NO 9 | BH1 | Unknown causal | AGCACGAGCTCACAGAAACTGCGAGAAGGACACCA[C/T]GAACACACGGAGCAAAGTCCAGTACCTCTTGACTC |
| SEQ ID NO 10 | BH1 | Unknown causal | AGACAAATGGAGGCAACAGAGCATAGATGTGAGAC[A/G]AGTTCCAGGCCTGACGCAGCACGAAGGAGAAACTG |
| SEQ ID NO 11 | HH2 | Unknown causal | AGGAAGAATGGAATATTAAAGCAGCAGATTAGATT[A/G]CAGGTAAAACCACCTTGGCCAGGGGGACTACAGCA |
| SEQ ID NO 12 | JH2 | Unknown causal | ATATAGTAGAGAAATATACATGTCTCAGACCACCC[C/T]TCCTCCTCTGATGGGCCCAGGTACATGAATTTTTT |
| SEQ ID NO 13 | HH2 | Unknown causal | ACTGATCTAATCTGACCCATTGGCCTTTTTTTTTT[A/T]AATTGAGCTTGCATGAGCTGTTAATGTATTTTGAA |
| SEQ ID NO 14 | HH2 | Unknown causal | ACTCCTACTGAGTCAACTGTAAATACTGTGTATCT[C/T]AGAAGTTAATTGTCAGTAAAAAACACATGAGCACA |
| SEQ ID NO 15 | HH3 | Flanking | TAGGACATGATACATGTTGGGTAAAGCAAAAGGCC[A/G]TGCCAAAATTCATATTGTTAAAAAGAAACTTGAGG |
| SEQ ID NO 16 | BH1 | Unknown causal | GTGCTCATCCAAGGGTGTTCTGAGCAGGAAAGGCC[A/G]CTGGTCAGGCAGCCCAGAAGGTGAGTTTGCCCATC |
| SEQ ID NO 17 | BH2 | Flanking | CTGACAGAATACTTGAATACAGGCAGAGCTTGCAG[A/G]TTTTGCATGCTTGGTTCCAACCACCACAATAAAGT |
| SEQ ID NO 18 | BH1 | Unknown causal | TGCTGCTCAATGTTCCCAAATTGTGTGCCACCAGA[A/G]GGCCTGATTTTGCAGGGAAAAGAGAAGTGGGTCCC |
| SEQ ID NO 19 | BH1 | Unknown causal | AGTGCTGGCCACCGCTGGACAATCAGCCTGAGGCC[A/G]GAGCTTGGAGGAACAAAGTCCAAGGACCGCAAACA |
| SEQ ID NO 20 | BH1 | Unknown causal | CTCCTGGCTGGGGCTGGGTGGCTGCAGGGAGGTGA[A/G]TCTGGGGCCAAGGTTAAAGCACCTGTAGACATTTC |
| SEQ ID NO 21 | HH2 | Unknown causal | CTTCCGGTGATTGAGGGTTATAAAAATGCCATTTA[C/T]CCAGCAAGGATGGTCATGTGAATTGGAGACTGATC |
| SEQ ID NO 22 | JH2 | Unknown causal | AGTAAATCTCTCAAACAAGTTTATAACCGTGGCCT[C/G]CACAAAAGGCATCAAATCTGGGTCTCGCATGAAAA |
| SEQ ID NO 23 | HH2 | Unknown causal | TTCATTCTGGTCTCTGCTTAAGTGTCATCTCCCCA[A/G]AGAGGCCTTTTTGGCCACCCTATGTAAGGAGAGT |
| SEQ ID NO 24 | BH1 | Unknown causal | AGGCATGGCTCCCTCCACATAAACACAGAGCCTCA[C/T]AGCAAGGCCAGAACCTATAGGCAAAGGGAGTTCAA |
| SEQ ID NO 25 | BH1 | Unknown causal | CACCCCCTGCCAGCCTAAGTGGCTCCTAACCCCTC[A/G]GTGCATCACCTATAAGGCCTGCACACAGGCACAAA |
| SEQ ID NO 26 | HH4 | Flanking | ACAGGAGAAGGGAGAGAACACTGGCAGGCACTAAC[A/G]TATCCACTTTATCTACAGTGCTGTAGCTTTTAGTT |

(56) References Cited

OTHER PUBLICATIONS

Tong "Generating gene knockout rats by homologous recombination in embryonic stem cells," Nat Protoc. Jun. 2011; 6(6).
Ferré et al. "Review: Recent advances in bovine in vitro embryo production: reproductive biotechnology history and methods." Animal, Oct. 17, 2019.
Supharattanasitthi et al. "CRISPR/Cas9-mediated one step bi-allelic change of genomic DNA in iPSCs and human RPE cells in vitro with dual antibiotic selection." Scientific Reports. (2019) 9:174. www.nature.com/scientificreports.
Ross et al. "Epigenetic remodeling in preimplantation embryos: cows are not big mice." Proceedings of the 32nd Annual Meeting of the Brazilian Embryo Technology Society (SBTE); Aug. 16 to 18, 2018.
National Academies of Sciences, Engineering, and Medicine. 2017. Human Genome Editing: Science, Ethics, and Governance. Washington, DC: The National Academies Press.
Goszczynski et al. "Gametes from stem cells: Status and applications in animal reproduction." Reprod Dom Anim. 2019; 54(Suppl. 4): pp. 22-31.
Adams, et al. "Identification of a nonsense mutation in APAF1 that is likely causal for a decrease in reproductive efficiency in Holstein dairy cattle." J. Dairy Sci. 99: pp. 6693-6701. 2016.
Fritz et al. "An initiator codon mutation in SDE2 causes recessive embryonic lethality in Holstein cattle." J. Dairy Sci. 101: pp. 6220-6231. 2018.
Hikabe et al. "Reconstitution in vitro of the entire cycle of the mouse female germ line." Nature. vol. 539. Nov. 10, 2016.
Huo et al. "Revolutionize livestock breeding in the future: an animal embryo-stem cell breeding system in a dish." Journal of Animal Science and Biotechnology (2018) 9:90.
Cole et al. "Haplotype tests for recessive disorders that affect fertility and other traits." Aip Research Report GENOMIC3 (09-13). Updated Dec. 1, 2018. https://aipl.arsusda.gov/reference/recessive_haplotypes_ARR-G3.html.
Hayashi et al. "Generation of eggs from mouse embryonic stem cells and induced pluripotent stem cells." Nature Protocols. Vol. 8, No. 8. 2013.
Goszczynski et al. "In vitro breeding: application of embryonic stem cells to animal production." Biology of Reproduction, 2018, 0(0), pp. 1-11.
Morohaku et al. "Complete in vitro generation of fertile oocytes from mouse primordial germ cells." PNAS, vol. 113, No. 32, Aug. 9, 2016. pp. 9021-9026.
Pablo Ross Slides for IETS Jan. 17, 2020.
Bogliotti et al. "Efficient derivation of stable primed pluripotent embryonic stem cells from bovine blastocysts." PNAS, vol. 115, No. 9. Feb. 27, 2018.
McLaughlin et al. "Metaphase II oocytes from human unilaminar follicles grown in a multistep culture system." Molecular Human Reproduction, vol. 24, No. 3 pp. 135-142, 2018.
CA Office Action issued on Apr. 2, 2024, in related Canadian Appl No. 3, 189,774 filed on Jan. 19, 2023.

* cited by examiner

| | Haplotype | Hap Annotation | Seq |
|---|---|---|---|
| SEQ ID NO 1 | HH2 | Unknown causal | AAATTTTCAAAGGTAAGAAAAGTGGGAGTTTGTG[A/G]CTGCATGATACCAAATGAATACTGCAGGCATTTA |
| SEQ ID NO 2 | JH1 | Causal | TTAGACAGACCACTCAGGATGCCCCTGAAGGTT[C/T]GAAACCGTGACTTCAGGAGAGAGTTGGAGGAGAGA |
| SEQ ID NO 3 | HH2 | Unknown causal | ATTCTAAATCACTGGACCACCAGGGAACTCCTTAT[C/T]CAACACTTTCTTTGTAATAAAATGTTAGATAGTG |
| SEQ ID NO 4 | JH1 | Flanking | TCATTAGAGGGCTGTATCAATCATGAGCTTCCCATTCAATCCT[A/G]TTCCGAGATTCTTGCATGCTAGGAGTTGAATTTGA |
| SEQ ID NO 5 | HH2 | Unknown causal | CCCACAACAATCATGAGCTTCCCATTCAATGTGAC[A/G]TCAGTGAAGGCCACATGAGGAGTAGTGATGAGGTA |
| SEQ ID NO 6 | BH1 | Unknown causal | TTCTAAGTATATGCTGGCATTGTCCTCTTGATAA[A/G]AGGTGTCACTCATGTTGTGGTGACCAAAGCCTGCA |
| SEQ ID NO 7 | HH3 | Flanking | CACAGTTCTGTGCACCAGGTGTCAACAACTCCAT[A/C]CACACTCGGCTAAAGCATCGCTTTGCTGGTGTCTG |
| SEQ ID NO 8 | HH2 | Unknown causal | GTCTATTCCTGGAACTTTCCCCACTTCAGGGAACC[C/T]AGGAGCAGGATAGCAAACCCACCAATCATTCCAC |
| SEQ ID NO 9 | BH1 | Unknown causal | AGCACGAGCTCACAGAAACTGCGAGAAGGACACCA[C/T]GAACACACGGAGCAAAGTCCAGTACCTCTTGACTC |
| SEQ ID NO 10 | BH1 | Unknown causal | AGACAAATGGAGGCAACAGAGACATAGATGTGAGAC[A/G]AGTTCCAGGCCTGCAGCAGCAACGAAGGAGAAACTG |
| SEQ ID NO 11 | HH2 | Unknown causal | AGGAAGAATGGAATATTAAAGCAGCAGATTAGATT[A/G]CAGGTAAAACCACCTTGCCAGGGGACTACAGCA |
| SEQ ID NO 12 | JH2 | Unknown causal | ATATAGTAGAGAAATATACATGTCTCAGACCACCC[C/T]TCCTCCTGATGGCCCAGGTACATGAATTTTT |
| SEQ ID NO 13 | HH2 | Unknown causal | ACTGATCTAATCTGACCCATTGGCCTTTTTTTT[A/T]AATTGAGCTTGCATGAGCTGTTAATGTATTTGAA |
| SEQ ID NO 14 | HH2 | Unknown causal | ACTCCTACTGAGTCAACTGTAAATACTGTGTATCT[C/T]AGAAGTTAATTGTCAGTAAAAACACATGAGCACA |
| SEQ ID NO 15 | HH3 | Flanking | TAGGACATGATCATCCAAGGGTGTTCTGAGCAGCAAAAGGCC[A/G]TGCCAAAATTCATATTGTTAAAAGAAACTTGAGG |
| SEQ ID NO 16 | BH1 | Unknown causal | GTGCTCATCCAAGGGTGTTCTGAGCAGGAAAGGCC[A/G]CTGGTCAGGCAGCCAGCCCAGAAGGTGAGTTTGCCCATC |
| SEQ ID NO 17 | BH2 | Flanking | CTGACAGAATACTTGAATACAGGCAGAGCTTGCAG[A/G]TTTTGCATGCTTGGTTCCAACCACCACATAAAGT |
| SEQ ID NO 18 | BH1 | Unknown causal | TGCTGCTCAAATGTTCCCAAATTGTGTGCCACCAGA[A/G]GGCCTGATTTTGCAGGGAAAAGAGAAGAAGTGGGTCCC |
| SEQ ID NO 19 | BH1 | Unknown causal | AGTGCTGGCCACCGCTGGACAATCAGCCTGAGGCC[A/G]GAGCTTGGAGGAACAAAGTCCAAGGACCGCAAACA |
| SEQ ID NO 20 | BH1 | Unknown causal | CTCCTGGCTGGGGCTGGGTGGCTGCAGGGAGGTGA[A/G]TCTGGGGCCAAGGTTAAAGCACCTGTAGACATTTC |
| SEQ ID NO 21 | HH2 | Unknown causal | CTTCCGGTGATTGAGGGTTATAAAATGCCATTTA[C/T]CCAGCAAGGATGGTCATGTGAATTGGAGACTGATC |
| SEQ ID NO 22 | JH2 | Unknown causal | AGTAAATCTCTCAAACAAGTTTATAACCGTGGCCT[C/G]CACAAAAAGGCATCAAATCTGGGTCTCGCATGAAAA |
| SEQ ID NO 23 | HH2 | Unknown causal | TTCATTCTGGTCTCTGCTTAAGTGTCATCTCCCCA[A/G]AGAGGCCTTTTTGGCCACCCTATGTAAGGAGAGT |
| SEQ ID NO 24 | HH2 | Unknown causal | AGGCATGGCTCCCCTGCCAAGTGCTCCTAACCCCTC[C/T]AGCAAGGCCAGAACCTATAGGCAAAGGAGTTCAA |
| SEQ ID NO 25 | BH1 | Unknown causal | CACCCCCTGCCAGCCTAAGTGGCTCCTAACCCCTC[A/G]TGTGCATCACCTATAAGGCCTGCACACAGGCACAAA |
| SEQ ID NO 26 | HH4 | Flanking | ACAGGAGAAGGGAGAGAACACTGGCAGGCACTAAC[A/G]TATCCACTTTATCTACAGTGCTAGCTTTTAGTT |

Figure 1A

| SEQ ID NO 27 | HH3 | Flanking | TCATTTTCTTTGAAGGTCAATAGGGCCACTATCAC[A/G]TAAAATAAAAGTTACTTGGAAATAAGTTCTGTAAT |
| SEQ ID NO 28 | BH2 | Flanking | ATTAATAAACAGATACTTCTTTTCCATTTCACCA[G/T]AAGTCTTTTGTACTGCGTTTTAAAACTAGCTTTGT |
| SEQ ID NO 29 | HH2 | Unknown causal | GAGTGGAGGCAATAGTGGTGGCCTGCCTCCCTGCAAGTGGGT[G/T]AGCCTGCTTGCTGGGTCTATAGCAGGATGCCATTG |
| SEQ ID NO 30 | BH1 | Unknown causal | CAGCCACTCAGGCTCAGGTGGCCTAGCCCTCCCTGCAAGTGGGT[G/T]GAGCAGATGAGAGCCCGAAGGAAAGACTGAGCAT |
| SEQ ID NO 31 | BH1 | Unknown causal | CGGCCACGAGGAGATGCGGCCGTGCTCTTGGTAGTCC[A/G]CTTGGGTGCCAGGTGCACGTGCGCAGCCACAGCG |
| SEQ ID NO 32 | BH1 | Unknown causal | TACAGTGAGGCACCTTCCTCCACTGTCCGCCAG[C/T]ACAGGGCCCAGGACAGCAAGCTGACCGGCTCAGG |
| SEQ ID NO 33 | BH1 | Unknown causal | CAGCCAGGTGGACACAGATCTATATTCAGACCTTG[C/T]CCACTGAGGCCTCTTGATACTTAGCAATATTTCAT |
| SEQ ID NO 34 | HH2 | Unknown causal | CTGGCTGATCTCCCACAAGTGAGGGGCTTCACAG[G/T]GTACAGGAAGCTTCCCTGTAAGGGTGTGAGGCCATCAGT |
| SEQ ID NO 35 | HH4 | Flanking | ACAATGTGAACAGTACCGCAGTAGGCCTTTGTCC[A/G]GTGGAAAGCTCCTGTAAGGGTGTGAGGCCATCAGT |
| SEQ ID NO 36 | JH1 | Flanking | GTATTTAGCTACATTTATCTTTCCCAGGGAAAATT[C/T]CTGCTCCAAAGATTGGATAAGTGCCATTTTATGG |
| SEQ ID NO 37 | HH5 | Not sure | CAATTTATGAAGTGTGGGCCATATCACTACTTGTC[A/C]AAAGGAAACCTATGTTTAAAACTCAAAGGGGTTA |
| SEQ ID NO 38 | HH2 | Unknown causal | TCTTGGCTCTATCATAGAGCTCTCTATTTACTTCTTA[A/G]CCATCACTCTATTCCAAGCCACCATCATCTCCACC |
| SEQ ID NO 39 | HHP | Flanking | CCAGAGCAGTCAGTTCACCCCAGGCAGAGGCCAC[C/T]GGGAGACCCTGCTGCGTTGACTCATTACAGCGAAA |
| SEQ ID NO 40 | HH2 | Unknown causal | AGGGGAGATGGAGGATAGAGGAAAGTGTTTTGGCC[A/G]AAGGACTAGAGTGAGGCAAGACCCCAATTAAGAC |
| SEQ ID NO 41 | BH1 | Unknown causal | AGACCCAGAAAGAATAGAATGGCTCTTGGGGATAT[A/G]AGGTGGCCATCAAATTGAACTCATGAGCTCTAAAC |
| SEQ ID NO 42 | HH2 | Unknown causal | TGAGCCTTAGCCAGGTCCCAGGTCCCACACAGGCCTGAA[A/G]TCTACCACAGTCAACTCTGACACAACTGTAGGA |
| SEQ ID NO 43 | HH3 | Flanking | TACAGGTTGGTCTGGATACAAGAGTTGGCCCACAA[C/T]AGGAATTGAAGAAGCAGAGAATAGAAGAAGGCAGA |
| SEQ ID NO 44 | BH1 | Unknown causal | TGGCGGCGGAGGGACTGGAGGGGCACACGGTGGCC[A/G]CGTTACCGCCGTGTCTGCTCCCGGAGGATTAACTC |
| SEQ ID NO 45 | BH1 | Unknown causal | GGTGCGCGACGACGCGACACGGCACGGCCTGTTGGCACGGA[C/T]CTTCATGTGGCCGCTGGTCCTGGTCCATGGGCTGG |
| SEQ ID NO 46 | BH1 | Unknown causal | CACAGAGCTCACACAGCACAGGCCTGTTGGCACGGA[A/G]GCACTGCTCGGTTCTGCTCGTCTGACACTTAAGGCAT |
| SEQ ID NO 47 | HH2 | Unknown causal | CACATTTATTTGGGTCTGCATGATATGTCTCAAAT[A/G]TCTCCAGACTTGGCCTTTATTAAGCAAGTTCTACA |
| SEQ ID NO 48 | JH2 | Unknown causal | AGGAAATGACTCTCCCAGGCTCTGCATGATATGTCTCAAAT[A/G]TCTCCAGACTTGGCCTTTATTAAGCAAGTTCTACA |
| SEQ ID NO 49 | BH1 | Unknown causal | TTCCTAGAGACCCTGCTGTGGGTGGCCCAGGAAAAC[G/T]TCCAGAGAAGCAGGAATAACTCTAAGTGTAAGTCA |
| SEQ ID NO 50 | BH1 | Unknown causal | TGGTGAGTGTGGGGTGGGAATCTAGCTGTGTGGGGG[C/T]AGCTCCCAGATTCGGGGGCCAGTTGTGTCTGCTG |
| SEQ ID NO 51 | BH1 | Unknown causal | ATTTCTTAATAAACCACATGTACTTTCGCCAACCA[G/T]TGAAATGGTCCCCTTGTTCCCTTAGTTCAGGTAT |
| SEQ ID NO 52 | BH1 | Unknown causal | TTCTCCTACCCACATCCAAATCTCTGGCCTGCTCC[A/G]GGTCCCCAGCAGACACATCCTTACTGTGGAGACA |

Figure 1B

| SEQ ID NO | | | Sequence |
|---|---|---|---|
| SEQ ID NO 53 | BH1 | Unknown causal | AGCCTACTACTACCAATTCGAGGCCCAAAGCAAAC[A/G]GAGTCCCAGTATCTTAAGTTTGGAAAATGTGTCAC |
| SEQ ID NO 54 | BH1 | Unknown causal | CACCTGCCCCCACCCCTGACCCCGGCCTTTCCT[A/C]TTCCTTCTGATGATGATTCCAGTGACATTTCCAGC |
| SEQ ID NO 55 | HH2 | Unknown causal | TTGGGCTCAGGAGCCCTACTGGTGGGCCCAGGAC[G/T]CTTAATTCAGCAGAAGCTATTCAACCCTTGTCAAT |
| SEQ ID NO 56 | HH2 | Unknown causal | ATGGGCTCATGTATAGATGAGAGGTCTCATTGTT[C/T]CTAAATCCTCAGGAAGGCCTGCCTGCTGAGAACTT |
| SEQ ID NO 57 | HH2 | Unknown causal | CCAGATATGAGAGCCAGATGGAGGCTCTGCCTGG[A/G]AGCTTGGCCATGTTCAGGGATGCTCCAGCATCGT |
| SEQ ID NO 58 | HH4 | Flanking | CCTTCACCTGTGTTTTTTGCCTTTTTCAGGATC[A/G]AACCTCCAAGCTCTCATAGACAGCACTAGGGAGCC |
| SEQ ID NO 59 | JH2 | Unknown causal | ACAGTTGAGCATTCATGAGTTACAAGTTCCAAAG[C/T]CCCACAAGCTACGGCCTGTTCTCTAGACGTACTA |
| SEQ ID NO 60 | HH3 | Flanking | TGCCATTAACAGTCATGTTTTTAACATTTCTTC[A/C]TGAGAACACACGCTCAGAGATTTCAGTTCTAGTT |
| SEQ ID NO 61 | HH2 | Unknown causal | AATCCAATTTCTGCAAGCAAAAAGAGAAGAAGGAT[G/T]CGCCCTGTTGTTGGATGAGGCCAAACTGTTGACC |
| SEQ ID NO 62 | JH2 | Unknown causal | TAAAATCTCTGCAAGCAAAAAGAGAAGAAGGAT[G/T]GGGGAGAGAGCAGTTCAGGCAGCAGAAGAAGTTGAAAT |
| SEQ ID NO 63 | BH1 | Unknown causal | GGGACCCCATCCTGCCCTGACCTGAGAGACAGCCTC[A/G]GGTGGAGAGCCCTCAGTGCCAAACAGAACCCTGCTC |
| SEQ ID NO 64 | HH2 | Unknown causal | TATTAGATTTTAATTAATTGGTTCTATCCTACCT[G/T]ATTTGATTGGTGTTGATTGTTTTACAAGTTAA |
| SEQ ID NO 65 | BH1 | Unknown causal | TCCTTGGGGCTGGCCTTGCCAGGTCAATTCACC[A/G]GTCCTTTCTCATCTCGTACCTACTTTCCACACCGG |
| SEQ ID NO 66 | JH1 | Flanking | ATTCTTCCATTTTATTCTAGCATGTGTAAACTA[G/T]ATCCTAAATTTCCTGAGGCTACAGTTCCCATACTA |
| SEQ ID NO 67 | HH2 | Unknown causal | CCTTCTGGTAAAGGTGAAACCTGAGCCACCTGGCC[A/G]GAGTATCCAGGCACTGCTAGGTGAGGCTACCAAGG |
| SEQ ID NO 68 | HHP | Flanking | TGGGATTTTTGTTGCTTAGAAGAGGCCACTAAATCC[A/G]GGGAATGCTCTCTCCCTCTAGCCCTTCTCTCCCTC |
| SEQ ID NO 69 | BH1 | Unknown causal | AAGGGAGGGGCAGGTGCCAGGTGCCACCTCCTAAGGCCTCAC[C/T]GCTGAGATCACTCCAAGGGGTGTTCAGGTGTGGT |
| SEQ ID NO 70 | HH2 | Unknown causal | TTTCTAATATCTCTTCATTGCAGGAGTCCCTGGTC[A/G]AGGGCTGGTTTGATTGCCAATGTCATAATCTAAA |
| SEQ ID NO 71 | BH1 | Unknown causal | ATGGCTTAGGCCAAATTAGGTTCTCTTATGTCAAA[C/T]TTGCTGGCATATTGATTTGGGGCTTCGTAGATAACTGAAG |
| SEQ ID NO 72 | HH4 | Flanking | CCTGTCCTTTGCTAGTTCATCAACCATGACAAACA[G/T]TGTATATTGATTTGGGCTTCGTAGATAACTGAAG |
| SEQ ID NO 73 | BH1 | Unknown causal | GGCAGCAAGTGGCCAGGTGCCAGGCTCAAGATCC[C/T]ACCACCATGCTCTGCTGTGTGCTAAGTCACTTC |
| SEQ ID NO 74 | HH2 | Unknown causal | CAAGTCAGGGGCCCCCAGCCGCTGGGATCTAATGC[A/G]TGATGACCTGACGTGAAGCTGAGGTAACAATAACA |
| SEQ ID NO 75 | BH1 | Unknown causal | TGCAGCCCAGTCCCTAACAGGCAAGGACCAGTACC[A/G]GTCTATGGCCCGGGGTTTGGGAGACCCCTGCACT |
| SEQ ID NO 76 | HH2 | Unknown causal | TCTCAGTCAACCAGAAAGAACATCCAACAGCTATA[C/T]GGTAAGGATTAGTAGGAGACCTTAGAAATCAAAA |
| SEQ ID NO 77 | BH1 | Unknown causal | CATAGTAAAAATGTCACTACAGTAAATGTGTGAA[A/C]AGGTGGTGAAGGCCTTTTTCTTCCATCTTTGAA |

Figure 1C

| SEQ ID NO 78 | BH1 | Unknown causal | CTGCCATGTTCATATATGGGCCTGTGTCTGAC[A/C]GATCCCTACCAGGACAAGATGTATCAGCCTTC |
| SEQ ID NO 79 | BH2 | Flanking | AGTGGATTTCTCCTGTGTAGTGAAATAAGCCTTCCCC[G/T]GAGTAAGTAGGCTGGAACACTTCCCAGCTGATG |
| SEQ ID NO 80 | HH2 | Unknown causal | ATGAGTGCAGAAACATCTGAATCTTGTTCTGTAAG[C/T]GGGCCAGTCTCTTCATGTTTAACCAAATTG |
| SEQ ID NO 81 | HH2 | Unknown causal | ATGAATAATAAAATTTAGTAAACGCGGTGCTTTC[C/T]CTATTTCATATATTGGCAATTGCATATAACCATT |
| SEQ ID NO 82 | HH2 | Unknown causal | ATTCAATGTATTTCGCAAATCTCCTGACTTTTCTG[C/T]ATTTCAAATTTAATGATTACAACTGTGGTTGAAA |
| SEQ ID NO 83 | HH2 | Unknown causal | GCAAGAGTACTGGAGTGGGGTGCCATTGTCTTCTC[C/T]TGTACTAGGCCAGGTTCTTGAAAAATAATGCAGA |
| SEQ ID NO 84 | HH2 | Unknown causal | AAGCCCCGAAAGAGGAAACATTAAGTTCAGTGCAGTC[A/G]CTCAGTCATACCGACTCTTTGCGAACCATGAGC |
| SEQ ID NO 85 | HH2 | Unknown causal | GCAGACTCCTTGGTGCCTGCCAGATCTTGGAGGCG[A/G]CATGTAATCCTTTGTTTTGAGTTTGTTCAACAT |
| SEQ ID NO 86 | JH2 | Unknown causal | TGTGTAGGCTGTACAAATTGATTTCTGTCCAAAGA[A/G]CAGAGGATGGAAAGGTGGGCGGAAAGTAACTTTAC |
| SEQ ID NO 87 | HH2 | Unknown causal | AACCCATTACACTTGAATATCTGAATTCTTGCCAAT[A/G]CATAATTTAAAGTCTTCACTTCAAAATAATTTGGT |
| SEQ ID NO 88 | HH5 | Not sure | CTAACTTTATTGACTTTAAAGGATTTCCATCATAG[C/T]GTGTAATTTTGCAAAATTTTGTGCATATTTCTGTT |
| SEQ ID NO 89 | HH2 | Unknown causal | CCAGTTCCATGGAGCTCTTGATCTTCAGCCTGTCC[A/G]ATGCCTCCTTTGTGGCACCACCCAGGTCTCT |
| SEQ ID NO 90 | HH2 | Unknown causal | CACTTGTAAAATGCCATTTTTTCTATAGAGATGT[A/C]TGATTTTCAGACTTTATATATTCTGGATATGAGT |
| SEQ ID NO 91 | BH1 | Unknown causal | CCTAGTCGATGTCCGTGAAGCCCTCAGTGTGAT[A/G]GCATACCGTGTTCTGTCAATGTTCTCCAGACA |
| SEQ ID NO 92 | HH2 | Unknown causal | CAAGAGACAGGATAGTAAATAAAGGGCAGACTGTG[A/G]CATTTAAATCTTTCAAAAAAGATGTCATCAGCTC |
| SEQ ID NO 93 | HH2 | Unknown causal | AGCCTCTCCTTCCTGCTGACCCTCGTTTCACCACAC[A/G]ACTGTACCCCAAATGCTGTTCAACTTAGGCGGACC |
| SEQ ID NO 94 | BH1 | Unknown causal | AGGCTGAGGGGTGCCCAGATGGAGAACTGAATGAA[A/G]GCAGTCAAGTGGTATAAAGTTCCAGTACAAGATA |
| SEQ ID NO 95 | BH1 | Unknown causal | ACTTTCATTTATTGCAGAATTTTATTATTGCTGT[A/G]TCCCATGAAAGTGAATTGAGCAAGGAGTAATGAGA |
| SEQ ID NO 96 | BH1 | Unknown causal | TGCCCTGGGATGATGGGCAACACTGGCCACTTAC[C/T]CTGTCTGCTGTGTGAGTTTAGATGAATGAGCAGTAC |
| SEQ ID NO 97 | JH1 | Flanking | TTTTTTAAGATGTCTCTGCTTTGTAGTGTTAG[C/T]CTGTCTGTCTGCTGTGAGTTTAGATGAATGAGAG |
| SEQ ID NO 98 | HH1 | Flanking | ACCAGGGAAGTTCCTGTACATTCTTAAATAGCTTTG[C/G]AAGATGGGATTCTGTGATGCTTGGGTATGAAAT |
| SEQ ID NO 99 | HH1 | Flanking | CACAATGAAGCTTGACTCTACCCAGGCCAGTAAGTTC[G/T]TGTGTTATCAGTTGGCACTCATTATCCTGGAATG |
| SEQ ID NO 100 | HH3 | Flanking | TTAACTCTAGATCTGAGATTCTGTCTTGGTTTC[A/G]CCATGATTCCTGGATTTAATTCGAGTACAAATTTA |
| SEQ ID NO 101 | BH1 | Unknown causal | TGCTATGGGCATAAGCCAGGAACCAGGAGCAGCACAGA[A/G]TTAGGGAGGGGCCTCGGGGTAGTGGTCAGAGGT |
| SEQ ID NO 102 | HH1 | Flanking | TAAATGCTTTACTTACTGTAATACATTGTAGTAGC[A/G]AAGAGCACTGTTTTGAAGCTACAAACCTAGGTTT |
| SEQ ID NO 103 | HH2 | Unknown causal | CTGGATAGTGACAGACTAGTATCAGGCATTCTTAC[A/G]TATGTCTAGCCAGGAGGGGGATTTTTTTTTTT |

Figure 1D

| SEQ ID NO 104 | HH2 | Unknown causal | AACATGGGGTGAATTAATAAATTTGCTTCTGAAAA[C/T]GCCGAGTTAACATAATGCAAGGACATTGCTATAG |
| SEQ ID NO 105 | HH2 | Unknown causal | GCCAGTGAGCTGCACTCTTGCTTCTTAGATTTCTGC[C/T]GAGTCCTATTATCACTCTGAAGGAACTGGCTGCTT |
| SEQ ID NO 106 | HH2 | Unknown causal | GATGTCTCAAAGCATGGGTGATGATAACTTAGTA[G/T]TTTAGATGCTAATGAAGCAGAAATCGAACCAGAAA |
| SEQ ID NO 107 | HH2 | Unknown causal | CATTATGGTGAAGTATTAGGGGGATAAATAAATAGA[A/C]AAGATAAGTAGGCTGCCAGACTGGGTGAGTTAGA |
| SEQ ID NO 108 | JH2 | Unknown causal | CAGCACACCAAATTCAGGTGATGATGACAGCTGTGCCC[A/G]GTCATCAGCTGTCCTTCTTGGAAGGACCATGAGAA |
| SEQ ID NO 109 | HH3 | Flanking | GTGTTGCCCTCTATAGCAACTTGAAAAGGTTATAAT[C/T]GTATTACCAAGAAAAAGAAATCAGACACATTTAGG |
| SEQ ID NO 110 | HH3 | Flanking | TATAAACATATGTACTTCATTTATAAAGAATTGCA[C/T]TGGTGAAGGAAAAAAATCTCTGACTAGCCTTGATAT |
| SEQ ID NO 111 | BH2 | Flanking | CTCATTATGATGAAAAAGCCACTCAAAGATTCGCA[C/T]TTCTCTCACTTCCTTCCGGATTAGGTTCATTATAGA |
| SEQ ID NO 112 | BH2 | Flanking | ACTGTTTTTAAGGGAAAAAACAATGCATGCCCTCGG[G/T]TATGGAGATGTTGAGTTGAGGTACACATAAGAGA |
| SEQ ID NO 113 | HH3 | Flanking | CTAATATTTTATTAGTATTGATTTCCCATTTGCCT[A/G]GTAGCCTAGTATTAGTGAATTCACTGAACTATTAC |
| SEQ ID NO 114 | BH2 | Causal | CCTGCTTGATATTCATCAGCTTCACACAGATCTTA[C/T]GAACAGCATCGTTCTCATGAACAAGGAGGGCGTCT |
| SEQ ID NO 115 | HH1 | Flanking | GTGTGTATAGGTATTCAAAGCTGAAACAGGAGAGA[A/T]ACTTCTAGAAATCAAGGCTCATGAGGATGAAGTGC |
| SEQ ID NO 116 | HH4 | Flanking | TGGCTGTAGGAATTGTCATCTCGTTCCACATACC[A/G]TGGGTGAAGGTTGGGCATGTGCTTTTCAGTTTTA |
| SEQ ID NO 117 | HH3 | Flanking | GACTTTGGATCTATTTTTTCTACTCTTTTGCCTGG[C/T]GCTAATGCTATGCTTGCACCACCAGAAGGGCAGAC |
| SEQ ID NO 118 | HH3 | Flanking | TCAGAAATTTGAGAATGCCTTTACTTCCAAGGTTCA[C/T]GATCTTTCAACTACACAACTGTTTCTAAAATATTA |
| SEQ ID NO 119 | JH2 | Unknown causal | TTAACCTAGGATATGAGGGTACAGGCTTGGATATA[A/G]GATGCATATTTCTAAGTAACAGATAACAGATAGGG |
| SEQ ID NO 120 | JH2 | Unknown causal | AGATACTGAGAAATATTTAATGAAGATAAAG[A/G]AACTCAAAACTGTGAGAATTCTCTATTAACAACTT |
| SEQ ID NO 121 | HH2 | Unknown causal | GTCTTATCTGCAAATTACTAAAAATAATCAGCTCT[A/G]AGAAGTGACCTTGGATGAAGCAGTATTAAATTGGC |
| SEQ ID NO 122 | HH2 | Unknown causal | CCTTACCTGAAAATTAGGAGTAAAATATTTAATAA[G/T]ATATCATCAATAAAAGACAATATCGAGTGCAATAC |
| SEQ ID NO 123 | HH2 | Unknown causal | ACCAAATGGCCAGTCGTGATGCTGAACTCAGTAAG[C/T]AGAATACATGAGCCTGGGAAACAAGATGTAAAAT |
| SEQ ID NO 124 | HH3 | Flanking | TATGTTTATTGTTTCTCTCTAAGCAGTCCATGTTA[C/T]TCTCCCCAAAGCGATTTTCCTTTCATTGCAGATATG |
| SEQ ID NO 125 | HH2 | Unknown causal | TCTTCTCTCAACTCCCTATCAAGCTTTGGCTGG[A/G]GTTTAGCTCCAGATGTTAGCCTCCACTAACTGGC |
| SEQ ID NO 126 | HH2 | Unknown causal | ACAGTCATTCCAGACAATGCATTCTTCAGTGATGA[C/T]GCAGTCTTGATATTATCAAAAGAAATGTTTATTTC |
| SEQ ID NO 127 | HH2 | Unknown causal | ACTTTTACATAACATGCCTGCAGAATAGAAGCAGG[A/G]ATTTTTTTTCTGGGAGATTATGAATTCTCATA |
| SEQ ID NO 128 | BH1 | Unknown causal | GCAGAGAGAAAGTCGGGCCTCAGCAGACAGCATGT[A/G]GAGTCTGGTTCCCGGAGCAGCCAAGACCCAGAAG |
| SEQ ID NO 129 | HH3 | Flanking | AGTCAGCTCTTTGCATCAGGTGGCCAAAGTGGCCAAAGTATATAAT[C/T]CATATTATTAATTAATGGTATATAAGGGCATGTGAGTT |

Figure 1E

| SEQ ID NO 130 | HH2 | Unknown causal | GAATAGAATCAGGAGAGATTTTGAAGGAGGAGTGCAT[C/T]ACAGTATTAAGTGTGGCTAAAAAGATAAGAAGGAT |
| SEQ ID NO 131 | HH2 | Unknown causal | CATTTGTGTATATTACCAGTGCATATATTAGCAGC[A/G]TTTTCTAGGCTTCAGGAAATGCTTCTAAAATTACT |
| SEQ ID NO 132 | HH2 | Unknown causal | TACATTGCGTGTGTGTGTGTGCATTTAGACACAC[A/G]TTTAGAAGACAAAATGTCAAGAAGAGCCTCGAGA |
| SEQ ID NO 133 | HH2 | Unknown causal | TAAAGTTTTAGTAGAAGAACATTAGGATGTGTATA[A/G]AAAAGGAAGAAGAATGGGCAGTCATATCAAGAAAGTAT |
| SEQ ID NO 134 | HH3 | Flanking | AGGTGGGAAGGAGGCACTGCAAATAGAATTCCTGG[A/G]GCTTTCAATCAGGCCAGAGAGAGGACATTGTGGGG |
| SEQ ID NO 135 | BH1 | Unknown causal | GACTAGAGGACATGGGCAGCGTTCTGGACATCAGG[C/T]AGTGACCATGGGCTCCCTGCCCTGATGGCCGGCAC |
| SEQ ID NO 136 | JH2 | Unknown causal | TCTAACTTGAAACTTATAACGGGCATGTTTTTCTTT[G/T]GGGGGAAGAAAAAAAGCCTAAAATCATGACTGAATC |
| SEQ ID NO 137 | BH1 | Unknown causal | GAAATCCACAAATCCACAGTGAGTTTTAAAAACTG[A/G]GCAAATAAATGGGTAAAGTAGAAAAGTCTTCCTT |
| SEQ ID NO 138 | BH1 | Unknown causal | GGATGTACGAAAGTCAAGGATGATGTTAGTGCTTA[C/T]GATGAGTGTGTCTAACTAGAGGATTTATTTCTCAC |
| SEQ ID NO 139 | BH1 | Unknown causal | AGGAAGAGAAACCCCAGACAAGTAAACAGAGGAAGGT[A/G]TCAGAAAACAGGATGATGTCTAATCATGAATCGCA |
| SEQ ID NO 140 | BH1 | Unknown causal | CCAGCAGTATGAAATCAGAATTAAAGGTCTGAAAT[C/T]CCCATGCCATGATGAATGTGTTCTTAACTATTAA |
| SEQ ID NO 141 | HH3 | Flanking | GGACCCTACCAACCGGTAAATACCTCCAGCCCTC[A/G]CCTTTGTGGTGGCAGACTTGAGATTGTGTCCCG |
| SEQ ID NO 142 | BH1 | Unknown causal | AGACTTGACCTTTATATATCTGGTAATGTCTAGA[C/T]TGTTGATTATTCCCTGGGCTAGGAAGAACTGGAA |
| SEQ ID NO 143 | HH2 | Unknown causal | GGACATAGGGACAGGGGAGGAGGACCAGACCAA[C/T]AGGTAATAGTAACTACCCTCACTGTTTCATCAACC |
| SEQ ID NO 144 | HH2 | Unknown causal | GGGCTTTCACACATTGCAAAGAAGAAAATCAGTCACAA[C/T]AAAAACTGCCTGATGAGAGACTGTTGCACACTTTG |
| SEQ ID NO 145 | BH1 | Unknown causal | GAGCCAGGGCTCCAGGAGGAGACAGATAGAAACTGCACCC[C/T]GCCCCCAACTTCCTGACTGAAGGCTGGATCGCCCT |
| SEQ ID NO 146 | HH2 | Unknown causal | TTCTTTCAAATGAACATTGTAAAAATATGAACTAG[G/T]TTTCAACTTAAATTGAAAACAAAATTAGGAACAT |
| SEQ ID NO 147 | HH2 | Unknown causal | TTATCTGTTTTTGCTCATCTTAATATAAAAATCTT[A/G]ACAGTTATGGTTCGAGTTCACCTGATGAGATTTC |
| SEQ ID NO 148 | HH2 | Unknown causal | TTCCATAACTTAAAAGGACCATATGTTCATTGAGA[A/G]GGAATTACTAGAAATGAACGTAATTTTTCTTC |
| SEQ ID NO 149 | HH2 | Unknown causal | GATATTAGCTGGTTTTAAATGTATTTTAACCTTT[A/G]GTGGTCGTTATTAAATTTTAACATAAAATTCAAA |
| SEQ ID NO 150 | HH2 | Unknown causal | GGAGTGTATTATAATGATTTTTCTATACTATTTGT[A/G]TTCTTAGTCACTCAGTCATGTCCGACTCTTTGCAA |
| SEQ ID NO 151 | BH1 | Unknown causal | CCCCTCTGACCTTCTCACTCTCCAGTCAAACCAGA[C/T]GTCTTCTCCAGCACGGTCCCTTCACTTATATCAG |
| SEQ ID NO 152 | BH1 | Unknown causal | ACCTCAGGGAGAAATAAAAGGTGATTGTTATGGCCCT[G/T]CCTGATTCCAGCAGCCCTGGGTCAGATGCTTCCCA |
| SEQ ID NO 153 | HH3 | Flanking | ATAAAGAGTTGGACAGGACTGAAGTGACTGAGCAT[A/G]CACACACTCAATCAGTATATATTTGAATTATTA |
| SEQ ID NO 154 | HH2 | Unknown causal | TTACCAGCGTTGTTAAACGCTGCCTGTGTTTCATT[C/T]TGCTTTGATGCTATTGAGGTAGCATGCCAGCAGA |
| SEQ ID NO 155 | HH2 | Unknown causal | TAACGTCGCTTTCCTCCTCAGTTTCTGTAGCTCTGAA[C/T]AGGGGGATAATAACAATATCTTCCTCAACACTTGTA |

Figure 1F

| | | | |
|---|---|---|---|
| SEQ ID NO 156 | HH2 | Unknown causal | CCTACAAACAGGCATGCTTGCCATCAATTGTAAAA[C/T]GTCTATATCCCCAAGCCCAGGATTCCTCCTAT |
| SEQ ID NO 157 | HH2 | Unknown causal | CTTTGATGCCATTATTACCATTGGTGACTCTGTG[A/G]TCAGCAAATGTTTGTCAATTAAAGTCTGAATC |
| SEQ ID NO 158 | HH2 | Unknown causal | ATATTTTGACATTAGCAAAAACTGCTTAGAGGT[A/G]GATTGCTACTAATATCATATATTTAATACTGTCA |
| SEQ ID NO 159 | HH2 | Unknown causal | GGAAGAAAAGTTTTTTTTTCTCTAATGAACATACTAAA[C/T]GACCCTGTAAAGGTGCACACAATA |
| SEQ ID NO 160 | HH2 | Unknown causal | CTGCACTGTAAGCCAGCTGTCATGAACATACTAAA[C/T]TATGTCATTGCCTATCGCTTTTATAGCATCCTA |
| SEQ ID NO 161 | HH2 | Unknown causal | AGACAGTAAATTAATTATAAGGTCATGTCAACAGA[A/G]AAGTAATGCACAAGACAAACAGCTCTTTATGTAAA |
| SEQ ID NO 162 | HH3 | Flanking | GCAACATGCCACAGAATGTGTTCATGGAGTCACA[A/G]ATGGGCAGGAAAAAAAGATAGACTAGAAATGACCA |
| SEQ ID NO 163 | BH1 | Unknown causal | TAAAAGTGCTAAAATTTGTAACTACTTTCCAATTA[C/T]ATTTAACCCCAGGTATGTACTATTTCATATTTA |
| SEQ ID NO 164 | BH1 | Unknown causal | TAGTTAACATTGACTAAGGGTTGGAGGCGGCCAAT[A/G]GACCCTCGAGAACAAGTATAAGCTTGTACTTCTCTG |
| SEQ ID NO 165 | BH1 | Unknown causal | CACTTTGCTCATGGGAGTATATGTGTATGGAGTA[C/T]GTC |
| SEQ ID NO 166 | JH2 | Unknown causal | CATGTTTAGGTAAGGAGGTGGGTAAGAAAACTGTTAAAATGTATTCA[C/T]GATGCCACTTCCCTTACTGGTGCAGTTTGCCCA |
| SEQ ID NO 167 | JH2 | Unknown causal | GAAGCAGAGATGGGTGAGGGTCTAAACCAGGAGA[G/T]GAACTAGACCTTCAGACCTGAAGGTTATCTGATTC |
| SEQ ID NO 168 | BH1 | Unknown causal | TTTGGAGAATTCTGTGCCTTTTCATATCCTCTCT[A/G]CTCTTTTCCTCCACACTGAGGGTCCAGTTGTTCT |
| SEQ ID NO 169 | BH1 | Unknown causal | AGACCAGTGAGGAGAGCACTTTATGGAAGGAAGAGG[A/G]AATTGTGAACGCTTGAGGGCTGCAGTCCAGGTCCAGCCCATGAGGCTGCC |
| SEQ ID NO 170 | HH3 | Flanking | CAAGGGAAGGAGAGCACTTTATGGAAGGAAGAGG[A/G]ATTGTGAACGCTTGAGGGCTGCAGTCCAAAGAGCCCTTGG |
| SEQ ID NO 171 | BH1 | Unknown causal | CCCCCTGGGTGCCTAGGGCTGATGGGTCTGACCCA[C/T]TGGATGGAACGCTTGAATCCAGAGCAGTGCCAG |
| SEQ ID NO 172 | JH2 | Unknown causal | AACTTTGTATCTACAGAAGTACTCTTCCTGGTTCATCCCC[C/T]TCATCTCTTGGGACTCACTCCAGTGATGCTGACT |
| SEQ ID NO 173 | JH2 | Unknown causal | GATGTTCTTTGCAACTGTTGTACCTGGTTGGTAGG[A/G]AATCATATAAAGGTGTGCTCCTGAGTTGGGACTCAAA |
| SEQ ID NO 174 | JH2 | Unknown causal | CTATTTGACACAGTGGCATGTAGACTAGGCAGTCA[A/G]ACAATGTTGTCTGTCCCTGAGTTGGGACTCAAA |
| SEQ ID NO 175 | BH1 | Unknown causal | GATGCAGAGACGTTTCAGGAAGGAGGCACTGCTAATATTT[G/T]TGATTTAGAAAAAAAATCACCCATTTATCATTC |
| SEQ ID NO 176 | BH1 | Unknown causal | AATGAGGGTAATTGCCTTTCATGTTCCATAATTTT[G/T]TGATTTAGAAAAAAAAATCACCCCATTTATCATTC |
| SEQ ID NO 177 | HH2 | Unknown causal | GGTACTTTGGGTTAACAGACTATTACATTGATGAC[A/G]TGCATTATTTGCCTCTGTTGCACTGATTAAAGGT |
| SEQ ID NO 178 | BH1 | Unknown causal | GCCATTTGTCTTGGGCCTAATCTTGTTCACGCAG[C/T]GTGGGAGGCTCCAACTGATCCCAAATTTCCCAAA |
| SEQ ID NO 179 | BH1 | Unknown causal | AAGAGTAGGGTACAAGTTTGGAAAGGGGCTTCTG[A/G]GGCCCCTATGGGGTGAGAAATACGAGTATGAGAGT |
| SEQ ID NO 180 | BH1 | Unknown causal | AAACATTTTCAGAATTGAATGTGGTCTATGTTCAC[C/T]TTTTCCTCTCATTTGGGGAACTTTCCCACTTCCA |
| SEQ ID NO 181 | BH1 | Unknown causal | TTCAGGGGAGTTCATTTGCAGGACCTGGAGGAAGA[C/T]GAGAGTATAGGAAGTCAGAATGCAGAATGAGGCTTGTGGGGA |

Figure 1G

| | | | |
|---|---|---|---|
| SEQ ID NO 182 | BH1 | Unknown causal | GTAGAAAACTTGATGTTTGCAACTTGATGTTTTTGGT[A/G]AAAAGTATATACCCATGAAATCATCATCACTATCA |
| SEQ ID NO 183 | JH2 | Unknown causal | AAAAGACTGTGTACACTCACTTGAATTTGCTTTCC[A/G]TTCTGTAAAAGGAGAGAATACGTTCTATTGTTTGT |
| SEQ ID NO 184 | HH3 | Flanking | AACCATTCTCTCATCAACGTAAGATAGATTAATAG[A/C]TTGCTAAATGCAACAGGATTTAATGTGAGTAGGCA |
| SEQ ID NO 185 | HH2 | Unknown causal | TCCACCACCTGGAGGCCCCTCCAGCTGCTAGTTTA[A/G]TCTTGGAGAGCATGATCTTAAACCACTAGCCTAT |
| SEQ ID NO 186 | HH3 | Flanking | AATGAAAATGTTATTATGGAGAAGAAGTTGAAACAG[A/C]AGCCAGAAAACTTAAGCTGGCCAATACCTTAATA |
| SEQ ID NO 187 | BH1 | Unknown causal | TTCCAGTACTACAGTTTAAAAGAACGAATTCTTCC[A/G]CGTTCAGCCTTCTTTAGGGGCCAATACTCACGTCA |
| SEQ ID NO 188 | BH1 | Unknown causal | CCCACTTTTCCGAATCCCATGTTCCAGCATCCAGCC[C/T]CCTTCACACCAGCAGAAACAGATTCAGGCTGGGTG |
| SEQ ID NO 189 | BH1 | Unknown causal | TGAGTGTCTCCTTCTGACCTTCATGTCGTATGACC[A/G]ATTTGTGGCTATTTGTAATCCCTGCAATACACAG |
| SEQ ID NO 190 | BH1 | Unknown causal | GATCTTTTGCTTATTATTCATTATATCTTTATG[A/G]AATAGTTATCTGAACTCACTGTCATTAATCTGAAC |
| SEQ ID NO 191 | BH1 | Unknown causal | TTGTATTGCTATCTCTCCATAATAATTCAACTTTA[C/T]ACATCACAAAGGAGGAAACAGAGGGAATTTTCTCA |
| SEQ ID NO 192 | BH1 | Unknown causal | GGATGCCCAGAGAGCCCATCCAACTCTGATATTTT[A/G]GATCCTGCAGTCATCACTTTTCCTGCTGTATCA |
| SEQ ID NO 193 | BH1 | Unknown causal | GTCTCCTGCTGGGCCTGGGAGGGGCGTGGGGAAG[A/G]ACCATCAGGAGACTGAGCTGCAAAAGACCCCTGGC |
| SEQ ID NO 194 | BH1 | Unknown causal | AATAAGGCAGAAGCCCTAATAATTTTGAAACAACA[A/G]CAGCAATCACTACTGTTGCTCCTCGTGGCAAGCTAT |
| SEQ ID NO 195 | BH1 | Unknown causal | AAATCCAAAAAAAAGGGGGAGGATTGTAAAAGTA[C/T]TAGTTAAAAATAAAGATGAATTATTTCATCTGCTC |
| SEQ ID NO 196 | BH1 | Unknown causal | GTTGAGTCGGACATAGCTGCCCTTGGATCCTAGCC[C/T]GGCCCCTGGGCACATGGAACCGTGGTGTCCTGGTC |
| SEQ ID NO 197 | BH1 | Unknown causal | CTCACTGGCAGTTGGCTGCATTCAGTTCTGGCCG[C/T]GTGGGGTCTTCCTGAATTTCACCTTGGCTTCTAGC |
| SEQ ID NO 198 | BH1 | Unknown causal | GTTACTCTAACATGGGTGGGATTACAGGTGATGCT[C/T]GGCCTTCTCCCCCCCAGGTATTTTAGTGGTCT |
| SEQ ID NO 199 | BH1 | Unknown causal | CTGAGGCCCAGAGGTGATCTATGGGCCCTCATGGA[C/T]TGATGCAGTCTTGGGGAAGGGATGGACGAGTGGT |
| SEQ ID NO 200 | BH1 | Unknown causal | TTGCCGTCACAGGCTGCGTGCGTGGCCTCATCTGAGGCC[C/T]CTGTCTCACCGTTCAGTTTCCCATTCTTAACA |
| SEQ ID NO 201 | BH1 | Unknown causal | ACAGCATCTGGAATTCTTGAGTGGCAGTGCAGCC[A/G]AGCTCGGACTCTGAGGCCAGACTCCGGGGTTCAAG |
| SEQ ID NO 202 | BH1 | Unknown causal | TCTCTGGATTTCCAGCACCCTAGACTGTTGCCAAA[A/C]TTGGCTCCATGTGCCTGGGAGGAGGTGCGGGCTG |
| SEQ ID NO 203 | BH1 | Unknown causal | ACAGAAAGATTTTAAAAGGCCAGCAATACTGTTCT[G/T]TAATTCAACATCAGCTCAGAGCTTTCTCATGTG |
| SEQ ID NO 204 | BH1 | Unknown causal | CACTGATCCCAGGAACCAGCAGCAGACACCAAGA[G/T]GTGACACACTCTATGGCTCATGAGAATAGAATAAC |
| SEQ ID NO 205 | BH1 | Unknown causal | ATCCCACTGAACACAGATGTTTGTTTCCTGCCATGGT[C/T]AGTCATGGCAAAAGAAATGCTAATCTTCTGCTATT |
| SEQ ID NO 206 | BH1 | Unknown causal | TCCCCCAGGAACACTTATATCATGAGTCCCAAGC[A/C]AAGAGGGCCTTCCCAGCTCCTCTAACATGGATCAC |
| SEQ ID NO 207 | BH1 | Unknown causal | AGGACTCATCAGCCCTGACCCTTACCTACTGTCAT[C/T]CTCAATCTTAGGCCCTTCTCATATCCATTTGTCCT |

Figure 1H

| SEQ ID | Label | Type | Sequence |
|---|---|---|---|
| SEQ ID NO 208 | BH1 | Unknown causal | TTTTAAAGGGATAGCCTAAGGAACCCCACTTGAAT[C/T]CTTGGAGGAGGGCATGGTTTCTGCATTGAGCCTGG |
| SEQ ID NO 209 | BH1 | Unknown causal | ACTTTCAGAAACCCATGTAAAAAACGATTATAAGC[C/T]CTGAACACAATGAATGTATCTGGGACTCCTGAGGG |
| SEQ ID NO 210 | BH1 | Unknown causal | GTGCATCACCAGGCCAGGATCCCTGGTCCAAAGCT[A/T]TAAAACAAGCTGGACACTCTTCCTCTTCTGAGCAC |
| SEQ ID NO 211 | HH1 | Flanking | TTTTCTTTTTAAGGTCTTTATTGATCTTGGATGAT[A/G]TTTGGGATCCTTGGGTGTTAAAAGCTTTTGACAAT |
| SEQ ID NO 212 | HH3 | Flanking | AGACATTTTTCTAAGAAAGATATAGTAAGGCCCAC[A/G]GGCATGGGATTAGATACTTAACACAGTAGTCATT |
| SEQ ID NO 213 | JH1 | Flanking | GCGGAGAGTCATGATGGCGTCTGTATGATCTCCGG[A/G]GGTAGCGGGTCGGAGTTCGGCCAAGTGAGCGGC |
| SEQ ID NO 214 | HH1 | Causal | GCCTCTGTGAACTGGAAACTTCAGAGGTTTATCGG[C/T]AAGCTAAGCTGCAGGCCAAGCAGGAGGTCGATAAC |
| SEQ ID NO 215 | BH2 | Flanking | GAGACGTATAGAATTCCTGGGTCCTTTGCATCTGGA[C/T]GGTTTGAATGGATAAAGCACCACTTGACAAATAAG |
| SEQ ID NO 216 | HBR | Flanking | AAGACGCTCCAAGAGGTGCTGCAGTGCTCCTGGTG[A/T]GGGTGGCAGTGCCGTCGTGTGCCCAGGCCTGTGA |
| SEQ ID NO 217 | HH3 | Causal | TACTCAGAATATTGGACATATGCTACGTACTCATT[C/T]CACACATTCTCAGGTAAGAACCAAAAGAGCCTCA |
| SEQ ID NO 218 | HH4 | Causal | GCTGACCAAGAACGGCCCCAAAGTTCTGGAATTTA[A/C]TTGCCGTTTCGGTGATCCAGAGTGCCAAGTGAGTA |
| SEQ ID NO 219 | JH1 | Flanking | TTATTAGCGTCCTTTGAGGGTGGGCTCTTGTGTT[A/C]CAGCATTTCTAAATTGTAACTTGGAAAAGATCTG |
| SEQ ID NO 220 | BH2 | Flanking | CGAGTGTGAATCTATAATATTACGGTACAACATAA[C/T]CTTCAATATTCATAACAGTACTCCTAAAGCAGGAA |

Figure 1I

METHODS FOR GENERATING, EVALUATING, GENE EDITING AND CLONING PLURIPOTENT STEM CELLS COMPRISING A LETHAL HAPLOTYPE

REFERENCE TO RELATED APPLICATIONS

This application claims the benefit of U.S. Provisional Patent Application No. 63/056,386 filed Jul. 24, 2020. The entire disclosure of which is incorporated herein by reference.

REFERENCE TO SEQUENCE LISTING

This application includes a sequence listing which has been submitted electronically in ASCII format and is hereby incorporated by reference in its entirety. Said ASCII copy, created on Sep. 8, 2021, is named Sequence ListingST-77US-02_ST25.txt and is 49,780 bytes in size.

BACKGROUND OF THE INVENTION

In livestock, recessive lethal haplotypes pose a significant problem for breeders, since a relatively large emphasis is placed on fertility, among other economic traits. Additionally, efforts by breeders to avoid producing offspring that are homozygous for these lethal haplotypes often result in suboptimal breeding values and slower genetic progress. Moreover, because certain lethal recessive haplotypes result in early embryonic death, studying and evaluating homozygous individuals has proven to be difficult if not impossible, thereby impairing the livestock industry's ability to develop more efficient breeding strategies and treatments using biotechnology.

SUMMARY OF THE INVENTION

One embodiment of the invention comprises a method of evaluating a bovine embryo comprising fertilizing an egg obtained from a first bovine heterozygote of a recessive lethal haplotype with sperm cells obtained from a second bovine heterozygote of the recessive lethal haplotype; producing the embryo from the fertilized egg, wherein the embryo is homozygous for the lethal haplotype; establishing a cell culture from the embryo; collecting a plurality of cultured cells; and obtaining omics data, comprising one or more features, from the plurality of cultured cells. A further embodiment comprises the steps of calculating feature weights for the one or more features; and calculating a production value, a genotypic value or a breeding value based on the calculated feature weights. In a particular embodiment, the recessive lethal haplotype is selected from the group consisting of: AH1, HH1, HH2, HH3, HH4, HH5, HH6, JH1, JH2, BH1 and BH2. In an even more particular embodiment, the step of establishing a cell culture from the embryo comprises culturing the embryo at the blastocyst stage. In a further aspect of this embodiment, the omics data is comprised of genotypic, proteomic or transcriptomic data. In a more specific embodiment, the step of establishing a cell culture comprises placing the embryo, or a cell sample from the embryo, on a first substrate in a first culture media comprising a base media (e.g. TeSR-E6 (Stem Cell Technologies, Canada)), a low free-fatty acid BSA (bovine serum albumin), Fibroblast Growth Factor 2 and an inhibitor of Wnt signaling for 11 to 14 days and thereafter dissociating cell outgrowths on the first substrate and placing the cell outgrowths on a second substrate in a second culture media comprising a ROCK (Rho-associated coiled-coil containing kinase) inhibitor. More specifically, in a further embodiment, the first substrate and the second substrate are comprised of irradiated mouse embryonic fibroblasts. In a yet further embodiment, the cell sample from the embryo comprises cells from the inner cell mass of the embryo.

Another embodiment of the invention encompasses a method of evaluating a plurality of bovine embryos comprising fertilizing a plurality of eggs obtained from one or more female bovine heterozygotes of a recessive lethal haplotype with sperm cells obtained from one or more male bovine heterozygotes of the recessive lethal haplotype; producing the plurality of embryos from the plurality of fertilized eggs, wherein the embryos are homozygous for the lethal haplotype; identifying a first group of one or more embryos from the plurality of embryos that are underdeveloped or dead after a first period of time; obtaining omics data from the identified first group. In a particular embodiment, the omics data comprises one or more features, and in a further embodiment comprises the steps of calculating feature weights for the one or more features; and calculating a production value, a genotypic value or a breeding value based on the calculated feature weights. An additional embodiment may also comprise the steps of identifying a second group of one or more embryos from the plurality of embryos that are underdeveloped or dead after a second period of time; and obtaining omics data from the identified second group. In a particular embodiment, the omics data is comprised of genotypic, proteomic or transcriptomic data. In an even more particular embodiment, the recessive lethal haplotype is selected from the group consisting of: AH1, HH1, HH2, HH3, HH4, HH5, HH6, JH1, JH2, BH1 and BH2.

BRIEF DESCRIPTION OF THE DRAWINGS

FIGS. 1A to 1I list SNP markers of lethal haplotypes.

DETAILED DESCRIPTION OF THE INVENTION

One aspect of the invention is encompassed by a method of generating pluripotent stem cells from an individual that is homozygous for a lethal haplotype. An additional aspect of the invention encompasses the use of gene editing to correct a causative mutation (including one or more base substitutions, deletions or insertions) of a lethal haplotype. A further aspect of the invention encompasses differentiating pluripotent stem cells comprising a homozygous lethal haplotype into other cell types in order to study the effects of the lethal haplotype. Finally, the invention also encompasses a method for determining the developmental stage or age of an individual when the effects of a lethal haplotype phenotypically manifest themselves.

Generating Zygotes/Embryos that are Homozygous for a Lethal Haplotype

In one embodiment of the invention, in order to generate or produce an individual, which includes a zygote, an embryo or a fetus, that is homozygous for a lethal haplotype, one first identifies a male carrier and a female carrier of the lethal haplotype. Carriers of lethal haplotypes can be identified by omics data, including but not limited to transcriptomic and genomic data, which may include DNA sequence data such as obtained by nucleotide sequencing and genotype data such as obtained using a single nucleotide polymorphism (SNP) microarray or nucleotide sequencing.

Examples of relevant lethal haplotypes in the bovine livestock industry that result in early embryonic death include but are not limited to Ayrshire Haplotype 1 (AH1), Brown Swiss Haplotype 1 (BH1), Brown Swiss Haplotype 2 (BH2), Holstein Haplotype 1 (HH1), Holstein Haplotype 2 (HH2), Holstein Haplotype 3 (HH3), Holstein Haplotype 4 (HH4), Holstein Haplotype 5 (HH5), Holstein Haplotype 6 (HH6), Jersey Haplotype 1 (JH1) and Jersey Haplotype 2 (JH2). Table 1 below lists the gene believed to be affected by each of these haplotypes.

homozygous zygote or embryo. Specifically, in certain aspects of the invention, in vitro produced zygote and embryos are produced in the laboratory by non-typical harvest of cattle oocytes, in vitro fertilization and embryo culture methodologies. In peripubertal heifers, prophase I immature cumulus oocyte complexes (COCs) are recovered from live standing females by using ultrasound guided transvaginal oocyte recovery (TVOR) system, also referred to as ovum pickup (OPU). In prepubertal heifers, ultrasound guided laparoscopic OPU is employed for COC recovery.

TABLE 1

| Haplotype | Result of homozygous haplotype | Affected Gene | Location of Mutation (chromosome no.: base pair region) |
|---|---|---|---|
| BH1 | Early embryonic or fetal death | unknown | 7: 42,811,272-47,002,161 |
| BH2 | Early embryonic or fetal death | tubulin delta 1 (TUBD1) | 19: 11,063,520 |
| HH1 | Early embryonic or fetal death | apoptotic peptidase activating factor 1 (APAF1) | 5: 63,150,400 |
| HH2 | Early embryonic or fetal death | unknown | 1: 94,860,836-96,553,339 |
| HH3 | Early embryonic or fetal death | structural maintenance of chromosomes 2 (SMC2) | 8: 95,410,507 |
| HH4 | Early embryonic or fetal death | Phosphoribosylglycinamide formyltransferase, phosphoribosylglycinamide synthetase, phosphoribosylaminoimidazole synthetase (GART) | 1: 1,277,227 |
| HH5 | Early embryonic or fetal death | transcription factor B1, mitochondrial (TFB1M) | 9: 93,223,651-93,370,998 |
| HH6 | Early embryonic death | SDE2 telomere maintenance homolog (SDE2) | 16: 27,833,776-29,661,958 or 16: 31,162,715-32,019,139 |
| JH1 | Early embryonic or fetal death | CWC15 spliceosome-associated protein (CWC15) | 15: 15,707,169 |
| JH2 | Early embryonic or fetal death | unknown | 26: 8,812,759-9,414,082 |

Additionally, FIG. 1 lists SNP markers for certain lethal haplotypes (SEQ ID NO 1 to SEQ ID NO 221). In FIG. 1, the SNP within each nucleotide sequence is denoted by brackets.

Each haplotype is identifiable in individuals through the use one or more genetic markers. These haplotypes are believed to be recessive, so only individuals with two copies of the haplotype (i.e., homozygous) will exhibit abnormalities. Individuals with only one copy, or no copies, of the haplotype will be normal. In the context of the invention, a haplotype may comprise one or more alleles.

One embodiment of the invention encompasses a method of producing a homozygous individual for a lethal haplotype in which gametes are obtained from a male carrier and a female carrier of the haplotype, and an obtained egg is fertilized with an obtained sperm cell in vitro to produce a When immature COCs are brought into the laboratory, they are placed into typical in vitro maturation (IVM) culture system where the most developmentally capable oocytes undergo spontaneous and programmed meiosis. After an overnight culture period, those oocytes that progress through meiosis I and accordingly shed their second polar body progressing to metaphase of the second meiotic division, and remain a plasma membrane intact and morphologically normal, those mature oocytes are placed into in vitro fertilization. Mature oocytes from individual females are placed into traditional IVF drops and mated to specific sires, using highly screened and accurate sperm capacitation treatments and sperm concentration per oocyte fertilized. Zygotes (day 1) are placed into traditional co-culture system and may be cultured to uterine stages of development by day 7-8 of culture.

In other embodiments of the invention, homozygous zygotes or embryos for a lethal haplotype are produced in vivo by traditional methods for synchronized supernumerary follicle production, artificial insemination and scheduled non-surgical transvaginal catheterized intrauterine embryo recovery (i.e., flushing).

As noted above, one aspect of the invention encompasses in vitro production of a homozygous individual for a lethal haplotype. By way of example only, the following oocyte maturation procedure, IVF procedure, in vitro culture procedure and co-culture procedure may be used with the invention.

Oocyte Collection. Collect slaughterhouse oocytes and wash 1× with about 3 mL Hepes washing media and with 1× with TCM-199 (Invitrogen, Carlsbad, CA)+10% Fetal Bovine Serum (FBS). Culture in maturation media for 22 hrs in a $CO_2$ incubator at 38.5° C. In one embodiment, the maturation media contains TCM-199, FBS, pyruvate, chorionic gonadotropin (e.g., Chorulon (Intervet, Summit NJ)), follicle stimulating hormone (FSH) (e.g., Folltropin (Bioniche, Belleville, Canada)), estradiol, and at least one antibiotic. In a further embodiment, Amikacin (Sigma-Aldrich, St. Louis, MO) can be used as the antibiotic. In another embodiment, the maturation media may also comprise luteinizing hormone.

In one embodiment, the maturation media may comprise 5-20 ml of TCM-199 Earl's; 0.5-2 ml of FBS (Thermo Fisher Scientific, Waltham, MA); 10-30 µl of pyruvate (prepared by adding 0.05-0.20 g of sodium pyruvate (Sigma-Aldrich, St. Louis, MO) to 5-20 ml of saline solution); 50-200 µl of chorionic gonadotropin (prepared by adding 5-20 UI of Chorulon (Intervet, Summit NJ) to 5-20 ml of TCM-199 Earl's); 5-20 µl of FSH (prepared by adding 0.001-0.01 g of Folltropin (Bioniche, Belleville, Canada) to 5-20 ml of TCM-199 Earl's); 5-20 µl of estradiol (prepared by adding 0.001-0.05 g of estradiol (Sigma-Aldrich, St. Louis, MO) to 5-20 ml of Etanol (Sigma-Aldrich, St. Louis, MO)); and 10-30 µl Amikacin (prepared by adding 0.1-1 g Amikacin sulfate salt (Sigma-Aldrich) to 20-40 ml of saline solution). In alternative embodiments, the maturation media may comprise the aforementioned components using different volumes but in the same proportion to each other, e.g., in one embodiment, the maturation media may comprise 10-40 ml of TCM-199; 1-4 ml of FBS; 20-60 µl of sodium pyruvate, etc. In a further embodiment, the maturation media comprises the above preparations of TCM-199 Earl's, FBS, pyruvate, chorionic gonadotropin, FSH, estradiol and an antibiotic in the approximate ratio of 9:1:0.02:0.1:0.01:0.01:0.02 by volume, respectively.

In Vitro Fertilization. Trim away cumulus cells from matured oocytes. Transfer them to a fertilization dish and return to the $CO_2$ incubator. Thaw frozen semen straws using standard procedures, centrifuge in 800 µL of Pure Sperm gradient (Nidacon, Molndal, Sweden), or a percoll or similar gradient at 2500 RPM for 10 minutes to remove egg components, glycerol and other debris. Remove supernatant, leaving a loose pellet of live sperm. Combine pellets using a small amount of fertilization media and repellet at 1500 RPM for 3 minutes. Carefully remove supernatant. Then gently mix the pellet. After determining the desired insemination dose, inseminate the oocytes by adding sperm to the pellet, then culture in a dish and return to the $CO_2$ incubator for about 18-22 hours.

In Vitro Culture. Remove presumptive zygotes from the fertilization dish and transfer into a sterile 1.5 mL eppendorf tube. Allow zygotes to form a loose pellet and remove excess media to form a 1:1 ratio of pellet and solution. Rinse the eppendorf tube with TCM-199, place contents into a dish and wash with BSA media. Then culture presumptive zygotes (discard disfigured oocytes, as well as oocytes with yellow colored cytoplasm or vacuolated cytoplasm) in a dual gas incubator (5% $CO_2$, 5% $O_2$) at 38.5° C. for about 48 hours.

Co-culture. Transfer cleaved zygotes to co-culture dishes comprising the cumulus cells from the mature oocytes and FBS media topped with mineral oil, and incubate in a $CO_2$ incubator at 38.5° C. until needed.

Generating Pluripotent Stem Cells from Embryos Homozygous for a Lethal Haplotype One embodiment of the invention encompasses a method for generating pluripotent stem cells that are homozygous for a lethal haplotype. One step of the method comprises producing an embryo that is homozygous for a lethal haplotype using gametes obtained from known carriers of the lethal haplotype.

In a particular embodiment of the invention, a hatched embryo is used to establish a pluripotent stem cell culture. Alternatively, the zona pellucida of an embryo (e.g., an expanded blastocyst) that is not hatched can be mechanically or chemically removed. Mechanical removal of the zona pellucida from an embryo can be accomplished in any suitable embryo splitting media using a needle or a laser, for example. Alternatively, the zona pellucida can be chemically removed, using pronase for example. In a particular embodiment of the invention, a 21G needle is used for mechanical separation of the zona pellucida from an embryo. In one embodiment, once denuded, the embryo is placed into a culture dish or well that is coated with mitotically inactivated feeder cells. In a particular embodiment of the invention, the inactivated feeder cells are comprised of irradiated mouse fibroblasts, and in an even more particular embodiment, are comprised of CF1 mouse embryonic fibroblasts (MEFs). In an alternative embodiment, the embryo is placed into a culture dish free of feeder cells. In certain embodiments of the invention, a culture dish free of feeder cells can be coated with a cell support material, for example, fibronectin, vitronectin or Matrigel (Corning Life Sciences, Tewksbury, MA).

The embryos are then cultured in a serum-free media comprising an inhibitor or antagonist of the Wnt/β-catenin pathway and either 1) a fibroblast growth factor (FGF) or 2) a member of the transforming growth factor beta (TGF-β) family or both. Examples of inhibitors of the Wnt/β-catenin pathway that may be used in the invention include, but are not limited to, inhibitors of Wnt response (IWR) including IWR1, IWR2, IWR3, IWR4 and IWR5 and inhibitors of Wnt production (IWP) including IWP1, IWP2, IWP3 and IWP4 and may be used a concentration of 0.5-5 µM, 1-4 µM, 2-3 µM or 2.5 µM. Examples of fibroblast growth factors that may be used in the invention include, but are not limited to, FGF1, FGF2, FGF3 and FGF4 and may be used at a concentration of 10-30 ng/ml, 15-25 ng/ml, 17-23 ng/ml or 20 ng/ml. Examples of members of the TGF-β family that may be used, include but are not limited to TGF-β1, Activin A and Activin B and may be used at a concentration of 10-30 ng/ml, 15-25 ng/ml, 17-23 ng/ml or 20 ng/ml. In a particular embodiment of the invention, the serum free media is comprised of an IWR and either 1) FGF2 or 2) Activin-A or both. In a more particular embodiment of the invention, the serum free media is comprised of IWR1 and FGF2. In another embodiment of the invention, the serum free media is comprised of IWR1, FGF2 and Activin A. In one embodiment of the invention, the serum-free media is comprised of TeSR-E6 (Stem Cell Technologies, Canada), although any serum-free media suitable for use in stem cell culturing may be used as a base media in the invention. In a particular embodiment of the invention, the serum-free media is supplemented with a serum protein, for example bovine serum albumin (BSA) at a concentration of 10-20 mg/ml, 12-17 mg/ml, 13-15 mg/ml or 13.4 mg/ml. In particular, embodiment of the invention, the BSA is comprised of a low free fatty acid BSA. The media in which the pluripotent stem cells are cultured may also comprise a suitable antibiotic, including but not limited to penicillin or streptomycin. In a particular embodiment of the invention, the serum free culture media comprises IWR1, FGF2, Activin A and BSA. In another embodiment, the serum free culture media comprises IWR1, FGF2 and Activin A. In a more particular embodiment, the serum fee culture media comprises TeSR-E6, IWR1 and FGF2; TeSR-E6, IWR1, FGF2 and BSA; TeSR-E6, IWR1, FGF2 and Activin A; or TeSR-E6, IWR1, FGF2, Activin A and BSA. In a particular embodiment of the invention, the serum-free media may be comprised of Dulbecco's Modified Eagle Medium: Nutrient Mixture F-12 (DMEM/F-12), examples of which include TeSR1 media disclosed by Ludwig et al. (Nature Methods, vol. 3, no. 8, August 2006, pp. 637-646); modified mTeSR1 media as disclosed by Wu et al. (Nature, 2015 May 21; 521(7552): 316-321), which lacked FGF2 and TGFβ1 but was supplemented with 20 ng/ml FGF2 and 2.5 µM IWR1; and N2B27 medium as disclosed by Tong et al. ("Generating gene knockout rats by homologous recombination in embryonic stem cells," Nat Protoc. 2011 June; 6(6)). In a particular embodiment of the invention, pluripotent stem cells can be cultured using a culture dish free of feeder cells and a serum-free media comprising FGF2, IWIR1 and Activin A. In an even more particular embodiment, pluripotent stem cells can be cultured using a culture dish free of feeder cells and a serum-free media comprising FGF2, IWIR1, Activin A and BSA.

Once the embryo is placed in a suitable culture media as above, the embryo is cultured at approximately 30-40° C., 35-39° C., 36-38° C., or 37° C. and with approximately 5% $CO_2$. After approximately 50-100 hours, 60-90 hours, 70-80 hours, or 72 hours, the culture media is replaced. If an embryo has failed to attach to the layer of feeder cells in the culture at the time the culture media is replaced, the embryo can be mechanically pressed against the bottom of the culture dish, using for example, a needle. After approximately 11 to 14 days in culture, any outgrowths are dissociated using trypsin or TrypLE (Gibco, Thermo Fisher Scientific, Waltham, MA) and passed to a new culture dish or well coated with inactivated feeder cells, and the composition of the media used to establish the initial cell culture may be used again in the replacement media. In a particular embodiment, this media is used to replace the initial cell culture media is supplemented with an inhibitor of Rho-associated, coiled-coil containing protein kinase (ROCK) at a concentration of 1-20 µM, 3-17 µM, 5-15 µM or 10 µM. In a particular embodiment, inhibitors of ROCK with which the media can be supplemented, include but are not limited to, Y-27632 and fasudil. In an even more particular embodiment, the media used to replace the initial culture media is supplemented with Y-27632. In a particular embodiment, ROCK inhibitor (for example Y-27632) is used in the culture media for 24 hours, and after 24 hours, the culture media is replaced with a culture media that does not comprise a ROCK inhibitor (for example Y-27632). On the day of the first cell passage (e.g., day 11) or at any passage thereafter, omics data may be obtained or extracted from for the cultured cells using a portion of the dissociated (i.e., unbound) cells or the culture media. In a more particular embodiment, dissociated cells may be genomically evaluated, by for example, genotyping with a SNP microarray or by DNA sequencing. In an even further embodiment, the genotype or DNA sequence may be analyzed for the presence of a lethal haplotype using one or more genetic markers for the lethal haplotype.

Omics Evaluation

In the context of the invention, "omics data" may include, but is not limited to, genomic, proteomic, transcriptomic, epigenomic, microbiomic or metabolomic data. In one embodiment of the invention, omics data is derived or obtained from molecules (small or large) or any other substances (ions, elements, etc.) obtained or extracted from a cell or tissue sample or detected in the cell or tissue sample. Additionally, omics data may be derived or obtained from molecules (small or large) or any other substances (ions, elements, etc.) obtained from fluid or media surrounding a cell or tissue sample. Both the presence and the quantity of such molecules or substances within a sample may be determined. Any known method in the art for detecting, measuring, quantifying or assaying molecules or other substances may be used with the invention, including but not limited to molecular hybridization, immunohistochemistry, real time quantitative PCR, quantitative reverse transcription PCR, blotting, nucleotide sequencing, protein sequencing, nuclear magnetic resonance spectroscopy, mass spectroscopy, liquid chromatography, gas chromatography and electrophoresis. In a specific embodiment, a transcriptome may be profiled using a microarray.

In a particular embodiment, transcriptomic, proteomic or metabolomic data can be derived from RNA, proteins or metabolites, respectively, found within a cell or tissue sample. Such a cell or tissue sample may be cryopreserved and then subsequently thawed for extraction of DNA or RNA or to obtain proteins or metabolites for profiling or any molecules providing omics data.

In one embodiment of the invention, omics data comprises features. For example, for metabolomic data, each assayed or measured metabolite can constitute a feature. In one embodiment, a feature may simply comprise the presence or absence of a particular molecule or substance, e.g., the presence of a particular metabolite or transcript, or alternatively a feature may comprise the quantity of a particular molecule or substance, e.g., the quantity of a particular metabolite or transcript. For example, the quantity of glucose in a tissue or blood sample can comprise a feature.

With respect to genomic data, in various embodiments of the invention, genomic data may comprise DNA or RNA-related data obtained from oligonucleotide arrays or other hybridization assays, DNA sequence data or RNA sequence data. In a specific embodiment of the invention, genomic data may be obtained from whole or partial genome sequencing using any technique known in the art. In addition to obtaining genomic DNA sequences, in other embodiments of the invention, RNA may also be sequenced, including messenger RNA (mRNA), precursor mRNA (pre-mRNA), transfer RNA (tRNA), ribosomal RNA (rRNA), non-coding RNA (ncRNA), long RNA, including long non-coding RNA (lncRNA) and small RNA, including micro RNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). In addition to sequencing such molecules, it is also contemplated that real time quantitative PCR or quantitative reverse transcription PCR may be used to quantify DNA or RNA in a sample.

DNA Extraction and Amplification

Another aspect of the invention encompasses sequencing or genotyping pluripotent stem cells homozygous for a lethal haplotype. In a specific embodiment, the DNA of cultured pluripotent stem cells can be used for sequencing or genotyping. Pluripotent stem cell DNA may first be extracted and then amplified (via PCR) so that there is a sufficient amount of DNA for sequencing or genotyping.

For genomic analysis, approximately 200 ng of double stranded DNA should be extracted per sample DNA at concentration per sample of 50 ng/ul. In certain embodiments of the invention, the DNA is used to confirm the presence of a lethal haplotype and/or confirm that the lethal haplotype has been corrected or suppressed via genetic modification. The remaining cells in culture remain in cell culture for passage and eventual harvest and cryopreservation for later diagnostic, cytogenetic and biological productive use such as gene editing and cloning.

By way of example, the following DNA extraction and amplification procedure may be used in certain embodiments of the invention. One skilled in the art will know that variations on this method exist and that this method should not be construed to limit the functionality or scope of the current invention. This method is illustrative only.

1.5 ml tubes containing a cell suspension of pluripotent stem cells are spun at ≥10000×g in a microcentrifuge for 45 seconds to pellet the cells. The suspension solution is pipetted off carefully so as to not remove the pelleted cells. Approximately 50 µl of suspension solution is left in each tube. The tubes are then vortexed for 10 seconds to resuspend the cell pellets. 300 µl of Tissue and Cell Lysis Solution (Epicentre; Madison Wisconsin; Catalog #MTC096H) containing 1 µl of Proteinase K (Epicentre; Madison Wisconsin; at 50 ug/µl; Catalog #MPRK092) is then added to each tube and mixed. The tubes are incubated at 65° C. for 30 minutes and vortexed at 15 minutes. The samples are cooled to 37° C. Afterwards 1 µl of 5 mg/µl RNase A (Epicentre; Madison Wisconsin; at 5 mg/ml; Catalog #MPRK092) is added to each sample and then mixed. The samples are then incubated at 37° C. for 30 minutes. The samples are then placed in a 4° C. cooler for 5 minutes. 175 µl of MPC Protein Precipitation Reagent (Epicentre; Madison Wisconsin; Catalog #MMP095H) is added to each sample, and the samples vortexed vigorously for 10-15 seconds. The samples are centrifuged in order to pellet debris for 8 minutes at ≥10000×g. The supernatant is transferred to a clean microcentrifuge tube. 600 µl of cold (−20° C.) isopropanol is added to the supernatant. Each tube is then inverted 30-40 times. The DNA is pelleted by centrifugation for 8 minutes in a microcentrifuge at ≥10000×g. The isopropanol is poured off without dislodging the DNA pellet. The pellet is rinsed once with 70% ethanol and then the ethanol is carefully poured off so as not to disturb the DNA pellet. The residual ethanol is removed with a pipet, and the DNA pellet is allowed to air dry in the microcentrifuge tube. Once dried, the DNA pellet is resuspended in 20 µl Tris-EDTA.

In certain embodiments of the invention, DNA from pluripotent stem cells can be extracted using the Purelink Genomic Kit Cat #K1820-00 (Invitrogen). In further embodiments, once the DNA is extracted, it can be put through a whole genome amplification protocol using the Illustra Genomiphi V2 DNA amplification kit (GE Lifesciences), which uses the phi29 DNA polymerase to amplify the genome.

Genotyping DNA

In one aspect of the invention, extracted and/or amplified DNA from stem cells may be genotyped using genomic single nucleotide polymorphism (SNP) arrays or chips, which are readily available for various species of animals from companies such as Illumina and Affymetrix. Alternatively, the entire genome can be sequenced using methods well-known in the art. Low density and high density chips are contemplated for use with the invention, including SNP arrays comprising from 3,000 to 800,000 SNPs. By way of example, a "50K" SNP chip measures approximately 50,000 SNPs and is commonly used in the livestock industry to detect lethal haplotypes and to establish genetic merit or genomic estimated breeding values (GEBVs).

Nucleotide Sequencing

One aspect of the invention comprises nucleotide sequencing extracted DNA or RNA. In certain embodiments of the invention, nucleic acid is extracted from pluripotent stem cells homozygous for a lethal haplotype, or that have been genetically modified, using any known method known in the art, including but not limited to Sanger sequencing and high throughput sequencing, which includes next generation (short read) sequencing and third generation (long read) sequencing. In one embodiment of the invention, one read with short read sequencing comprises approximately 100 to 300 base pairs, and one read with long read sequencing comprises approximately 10,000 or more base pairs. Non-limiting examples of sequencing methods for use in the invention include single-molecule real time sequencing, ion semiconductor sequencing, pyrosequencing, sequencing by synthesis, combinatorial probe anchor synthesis, sequencing by ligation, nanopore sequencing, massively parallel signature sequencing, polony sequencing, DNA nanoball sequencing, heliscope single molecule sequencing and sequencing using droplet based microfluidics or digital microfluidics.

Cryopreservation of Cells

The following method of cryopreserving cells may be used in the invention and is presented by way of example only. Any method known in the art for cryopreserving stem cells may be used in the invention.

Cells are washed twice with phosphate-buffered saline (PBS) and then incubated with prewarmed TrypLE Select (Gibco) at 37° C. for 8 to 10 minutes. Then, the cells are detached by gentle pipetting and the cell suspension is transferred to a conical 15 mL tube containing 5 to 10 ml of culture media and centrifuged at 300×g for 10 minutes. After centrifugation, the supernatant is removed carefully to avoid disturbing the pellet and cold (2-8° C.) CryoStor CS10 (StemCell Technologies) is added. After mixing thoroughly, the suspension is transferred to a cryovial. The cells are cryopreserved using a standard slow-rate cooling procedure; cryovials are placed at −80° C. in a styrofoam box for 24 hours and then stored in liquid nitrogen.

Genetic Modification

One aspect of the invention encompasses methods of genetically modifying stem cells of the invention. In particular, one aspect of the invention encompasses correcting or suppressing one or more mutations responsible for a lethal haplotype in a pluripotent stem cell and then 1) using the stem cell as a donor to create a clone or 2) using the stem cell to derive/generate gametes and then producing progeny from the gametes. In a particular embodiment, gene editing can be used to make targeted changes to gene sequences that remain after cell division. Clustered regularly interspaced palindromic repeats (CRISPR) and CRISPR associated endonuclease (Cas9) may be used to repair a mutated gene such as in lethal haplotype by providing a DNA template of the normal gene that can be incorporated through a process known as homology directed repair (HDR). Supharattanasitthi et al. demonstrated CRISPR/Cas9-mediated one step bi-allelic change of genomic DNA in induced pluripotent stem cells in vitro using dual antibiotic selection (Scientific Reports (2019) 9:174). In one embodiment, the method outlined in Supharattanasitthi et al. can be used to alter the genomic DNA of the pluripotent stem cells to correct or eliminate a lethal haplotype.

Cloning

One aspect of the invention encompasses cloning using a pluripotent stem cell of the invention as a donor. Mammals have been cloned using embryonic stem cells. See, e.g., Wakayama et al., Proc Natl Acad Sci USA, 1999 Dec. 21; 96(26):14984-14989. In a particular embodiment, a lethal haplotype is corrected/suppressed via gene editing in a pluripotent stem cell and then the cell is used as a donor cell in cloning. The following cloning procedure is presented by way of nonlimiting example only.

Oocyte Enucleation. In vivo matured oocytes are collected from donor females. Oocytes with attached cumulus cells or devoid of polar bodies are discarded. Cumulus-free oocytes are divided into two groups: oocytes with only one polar body evident (metaphase II stage) and the activated telophase II protocol (oocytes with one polar body and evidence of an extruding second polar body). Oocytes in telophase II are cultured in M199+10% FBS for 3 to 4 hours. Oocytes that are activated during this period, as evidenced by a first polar body and a partially extruded second polar body, are grouped as culture induced, calcium activated telophase II oocytes (Telophase II-Ca+2) and enucleated. Oocytes that have not activated are incubated for 5 minutes in PBS containing 7% ethanol prior to enucleation. Metaphase II stage oocytes (one polar body) are enucleated with a 25-30 micron glass pipette by aspirating the first polar body and adjacent cytoplasm surrounding the polar body (approximately 30% of the cytoplasm) presumably containing metaphase plate.

Telophase stage oocytes are prepared by two procedures. Oocytes are initially incubated in phosphate buffered saline (PBS, $Ca^{+2}/Mg^{+2}$ free) supplemented with 5% FBS for 15 minutes and Cultured in M 199+10% FBS at 38° C. for approximately three hours until the telophase spindle configuration or the extrusion of the second polar body is reached. All the oocytes that respond to the sequential culture under differential extracellular calcium concentration treatment are separated and grouped as Telophase II-$Ca^{2+}$. The other oocytes that do not respond are further incubated in 7% ethanol in M199+10% FBS for 5-7 minutes (Telophase II-ETOH) and cultured in M199+10% FBS for 2 to 4 hours. Oocytes are then cultured in M199+10%/FBS containing 5 μg/ml of cytochalasin-B for 10-15 minutes at 38° C. Oocytes are enucleated with a 30 micron (OD) glass pipette by aspirating the first polar body and approximately 30% of the adjacent cytoplasm containing the metaphase II or about 10% of the cytoplasm containing the telophase II spindle. After enucleation the oocytes are immediately reconstructed.

Embryo Reconstruction. Pluripotent stem cells are harvested by trypsinizing (0.025% trypsin/0.5 mM EDTA) (Sigma) for 7 minutes. Single cells are resuspended in equilibrated M199+10% FBS supplemented with 2 mM L-glutamine, penicillin/streptomycin. The donor cell injection is carried out in the same medium as for enucleation. Donor cells are graded into small, medium and large before selection for injection to enucleated cytoplasts. Small single cells (10-15 micron) are selected with a 20-30 micron diameter glass pipette. The pipette is introduced through the same slit of the zona made during enucleation and donor cells are injected between the zone pellucida and the ooplasmic membrane. The reconstructed embryos are incubated in M199 30-60 minutes before fusion and activation.

Fusion and Activation. All reconstructed embryos (ethanol pretreatment or not) are washed in fusion buffer (0.3 M mannitol, 0.05 mM $CaCl_2$, 0.1 mM $MgSO_4$—, 9 mM $K_2HPO_4$, 0.1 mM glutathione, 0.1 mg/ml BSA in distilled water) for 3 minutes before electrofusion. Fusion and activation are carried out at room temperature, in a chamber with two stainless steel electrodes 200 microns apart (BTX® 200 Embryomanipulation System, BTX®-Genetronics, San Diego, Calif.) filled with fusion buffer. Reconstructed embryos are placed with a pipette in groups of 3-4 and manually aligned so the cytoplasmic membrane of the recipient oocytes and donor CFF155-92-6 cells are parallel to the electrodes. Cell fusion and activation are simultaneously induced 32-42 hours post GnRH injection with an initial alignment/holding pulse of 5-10 V AC for 7 seconds, followed by a fusion pulse of 1.4 to 1.8 KV/cm DC for 70 microseconds using an Electrocell Manipulator and Enhancer 400 (BTX®-Genetronics). Embryos are washed in fusion medium for 3 minutes, then they are transferred to M199 containing 5 μg/ml cytochalasin-B (Sigma) and 10% FBS and incubated for 1 hour. Embryos are removed from M199/cytochalasin-B medium and co-cultured in 50 microliter drops of M199 plus 10% FBS with goat oviductal epithelial cells overlaid with paraffin oil. Embryo cultures are maintained in a humidified 39° C. incubator with 5% $CO_2$ for 48 hours before transfer of the embryos to recipient females.

The following alternative cloning procedure is presented by way of nonlimiting example only.

Remove COC's from maturation medium and rinse through one dish of warm TL Hepes (MOFA GLOBAL, Bovi Pro Oocyte Washing Medium with BSA at 3 mg/ml, filtered). Transfer the COC's into a hyaluronidase drop within the dish of TL Hepes. The cumulus cells of the COC's are stripped by hand, first by using a 200 μl gel loader pipet tip to remove the outer layers of cumulus, then by using a denudation pipet to remove the remaining cumulus cells. Those oocytes that are clean (no cumulus cells) are transferred to a second dish of warm TL Hepes. If there are eggs that still have cumulus cells attached, transfer those to another drop of hyaluronidase and finish hand stripping them, then transfer to the TL Hepes dish. The maturation rate (MO, mature oocyte) is determined by checking each viable oocyte for an extruded polar body (PB). Those eggs that are not mature need to be enucleated immediately.

To a nunc well, add 0.50 ml of Cyto B medium (2 ml TL Hepes and 1 μl Cytochalasin B (Sigma C-6762)) and 10 μl of Hoescht stain. Remove the oocytes from the maturation medium and rinse through warm TL Hepes, and then place the oocytes in the nunc well with the Hoescht stain for 15 minutes. At the end of the 15 minutes, rinse the oocytes through warm Cytochalasin B. Transfer to the lower drop of Cytochalasin B in a manipulation plate. Using the tip of a glass enucleation tip (25 μm inner diameter), pierce through the zona of an oocyte, carefully, bring your tip near to the chromosomes and slowly aspirate them out, taking as little cytoplasm as possible. When that oocyte is successfully enucleated move to a separate area of the dish and enucleate the rest of the oocytes. When you are ready to "reconstruct" (putting a cell into the enucleated oocyte), turn the UV light off, turn up the light to a comfortable level. Get an enucleated oocyte on the holder, using your tip, turn the oocyte until the "slit" made when enucleating the oocyte is in focus and in the same plane as your tip. Using the slit deposit one cell into the space between the zona and the cytoplasmic membrane of the oocyte to create a reconstructed embryo. Rinse all reconstructed embryos in TLHepes and then place into a maturation caffeine media (2 ml in vitro maturation media with 3.9 mg caffeine) until ready to fuse, at approximately 24 hours post maturation.

When ready to fuse (approximately at 23.5-24 hours post maturation), turn on the BTX machine (ECM Square Wave Electroporation System 830), making sure the settings are: mode LV, voltage 100, pulse length 40 μsec. Put the fusion chamber into the 100 mm dish, attach the red lead to the top wire, the black lead to the lower wire. Transfer reconstructed embryos in a dish comprising TLHepes. Pick up 8-10 reconstructed embryos and transfer to a dish containing a caffeine media (29.1 mg of caffeine in 15 ml of TLHepes) and let them sink. Transfer the 8-10 reconstructed embryos to another dish containing 2 ml of a SOR-based media (77.7 mg caffeine in 50 ml of SOR media) and let the sink. Finally, transfer the 8-10 reconstructed embryos to the fusion chamber, which is filled with the SOR-based media, and once the reconstructed embryos are lined up, hit "pulse" on BTX machine. Once fused, transfer reconstructed embryos back to the dish containing the caffeine media for rinsing and then to a dish containing TLHepes, until all reconstructed embryos are fused. When fusions are completed, transfer all fused embryos to a dish containing 500 μl of a CR1aa/CR2 media (comprising 9.7 mg caffeine/5 ml CR2) for 1 hour.

To activate, (at 25 hours, 1 hour post-CR2+ caffeine), place reconstructed embryos in a nunc well along with 500 μl of ionomycin media (3 μl ionomycin and 3 ml TL Hepes) for 4 minutes. Remove and rinse three times in a dish of warm TL Hepes. Transfer the activated embryos to a nunc well containing 500 μl of cycloheximide media (at a concentration of 10 μg/ml of cycloheximide) and return to the incubator for 5 hours. After the 5 hours, remove the lysed oocytes, and rinse the remaining oocytes 6 times through the center area of the nunc well and return to the incubator. This is Day 0. On Day 5, move all embryos that are less than 8 cells to another nunc well, (count the number of 1 cells, cleaved, 8 cells and morula), leave the 8 cells and morula, add 25 μl of warm fetal bovine serum (FBS 5%) to the well and return to the incubator. On Day 6 and Day 7, check for any embryos that can be transferred. If there are, using a 2 ml Sartstedt tube, put 1 ml of Minitube holding media (BoviHold, Minitub International) into the tube and warm. Once the media is warm, transfer embryos to the tube and send to the farm for embryo transfer.

Example 1

Embryonic Stem Cell Line Establishment

Five HH5 tested positive cows were submitted to artificial insemination (AI) by using frozen conventional sperm from a HH5 tested positive bull. 7 days post AI, the embryos were recovered by uterine flushing and then were sent to the cell culture laboratory. To establish the cell lines, hatched embryos were used, and the expanded blastocyst that were not hatched were submitted to mechanical removal of the zona pellucida with a 21G needle into a drop of splitting media (ABT 360, USA). Ninety four denuded embryos were used, each embryo was placed into an individual well of a 12 well tissue culture-treated dish (Falcon) coated with irradiated CF1 Mouse Embryonic Fibroblasts (MEFs) (Gibco) and cultured with TeSR-E6 (Stem Cell Technologies, Canada) as base media, supplemented with (13.4 mg/mL) Low Free Fatty Acid BSA (MP Biomedicals NZ), 20 ng/mL bovine FGF2 (bFGF2) (Peprotech, USA), 2.5 μM IWR1 (Sigma, USA) and 1× penicillin-streptomycin (Gibco), at 37° C. and 5% $CO_2$. After 72 hours, the culture media was changed for the first time, and the embryos that did not attach to the feeder layer, were mechanically pressed against the bottom of the well with a 21G needle, then the media was changed daily. After 11 days of culture, the outgrowths were dissociated using TrypLE (Gibco) and passed to a new well, previously coated with MEFs, and cultured in the same media supplemented with 10 μM Y-27632 (Enzo life science). The day of the first passage, a sample of cells was collected to be sent for qPCR analysis for HH5 (Genetic Visions, Wisconsin, USA). A total of 25 cell lines were established and sent for qPCR analysis, 5 of them, were confirmed homozygous. Two samples of the confirmed homozygous HH5 gene were genotyped using (BovineHD BeadChip assay 777k, Illumina Inc., San Diego, CA). These 2 embryos—cell lines, received a homozygous evaluation for HH5 by the Council on Dairy Cattle Breeding (CDCB). These are the first global published results showing this event.

What we claim is:

1. A method of evaluating a bovine embryo comprising:
fertilizing an egg obtained from a first bovine heterozygote of a recessive lethal haplotype with sperm cells obtained from a second bovine heterozygote of the recessive lethal haplotype;
producing the embryo from the fertilized egg, wherein the embryo is homozygous for the lethal haplotype;
establishing a stem cell culture from the embryo;
collecting a plurality of cultured stem cells; and
obtaining omics data, comprising one or more features, from the plurality of cultured stem cells.

2. The method of claim 1, wherein the recessive lethal haplotype is selected from the group consisting of: AH1, HH1, HH2, HH3, HH4, HH5, HH6, JH1, JH2, BH1 and BH2.

3. The method of claim 1, wherein the step of establishing a cell culture from the embryo comprises culturing the embryo at the blastocyst stage.

4. The method of claim 1, wherein the omics data is comprised of genotypic, proteomic or transcriptomic data.

5. The method of claim 1, wherein the step of establishing a cell culture comprises placing the embryo, or a cell sample from the embryo, on a first substrate in a first culture media comprising a low free-fatty acid BSA (bovine serum albumin), Fibroblast Growth Factor 2 and an inhibitor of Wnt signaling for 5-15 days and thereafter dissociating cell outgrowths on the first substrate and placing the cell outgrowths on a second substrate in a second culture media comprising a ROCK (Rho-associated coiled-coil containing kinase) inhibitor.

6. The method of claim 5, wherein the first substrate and the second substrate are comprised of irradiated mouse embryonic fibroblasts.

7. The method of claim 5, wherein the cell sample from the embryo comprises cells from the inner cell mass of the embryo.

8. A method of evaluating a plurality of bovine embryos comprising:
fertilizing a plurality of eggs obtained from one or more female bovine heterozygotes of a recessive lethal haplotype with sperm cells obtained from one or more male bovine heterozygotes of the recessive lethal haplotype;
producing the plurality of embryos from the plurality of fertilized eggs, wherein the embryos are homozygous for the lethal haplotype;
identifying a first group of one or more embryos from the plurality of embryos that are underdeveloped or dead after a first period of time;
establishing a stem cell culture from each of the embryos in the identified first group;
collecting cultured stem cells from each of the established stem cell cultures; and
obtaining omics data from the collected cultured stem cells.

9. The method of claim 8, wherein the omics data comprises one or more features.

10. The method of claim 8, further comprising the steps of:
identifying a second group of one or more embryos from the plurality of embryos that are underdeveloped or dead after a second period of time; and
obtaining omics data from the identified second group.

11. The method of claim 10, wherein the omics data is comprised of genotypic, proteomic or transcriptomic data.

12. The method of claim 8, wherein the recessive lethal haplotype is selected from the group consisting of: AH1, HH1, HH2, HH3, HH4, HH5, HH6, JH1, JH2, BH1 and BH2.

* * * * *

SEQUENCE LISTING

<160> NUMBER OF SEQ ID NOS: 220

<210> SEQ ID NO 1
<211> LENGTH: 71
<212> TYPE: DNA
<213> ORGANISM: Bos taurus

<400> SEQUENCE: 1
aaattttcaa aggtaagaaa agtggggagt ttgtgrctgc atgataccaa atgaatactg    60
caggcatttt a    71

<210> SEQ ID NO 2
<211> LENGTH: 71
<212> TYPE: DNA
<213> ORGANISM: Bos taurus

<400> SEQUENCE: 2
ttagacagac cactcaggat gcccctgaag aggttygaaa ccgtgacttc aggagagagt    60
tggaggagag a                                                        71

<210> SEQ ID NO 3
<211> LENGTH: 71
<212> TYPE: DNA
<213> ORGANISM: Bos taurus

<400> SEQUENCE: 3
attctaaatc actggaccac cagggaactc cttatycaac acttttctttt gtaataaaat   60 gttagatagt g                                                        71

<210> SEQ ID NO 4
<211> LENGTH: 71
<212> TYPE: DNA
<213> ORGANISM: Bos Taurus

<400> SEQUENCE: 4
tcattagagg gctgtatcaa taatcctcat atcctrttcc gagattcttg catgctagga   60 gttgaattg a                                                         71

<210> SEQ ID NO 5
<211> LENGTH: 71
<212> TYPE: DNA
<213> ORGANISM: Bos taurus

<400> SEQUENCE: 5
ccccaacaat catgagcttc ccatctcaat gtgacrtcag tgaaggccac atgaggagta   60
gtgatgaggt a                                                        71

<210> SEQ ID NO 6
<211> LENGTH: 71
<212> TYPE: DNA
<213> ORGANISM: Bos taurus

<400> SEQUENCE: 6
ttctaagtat atgctggcca ttgtcctctt gataaraggt gtcactcatg ttgtggtgac   60
caaagcctgc a                                                        71

<210> SEQ ID NO 7
<211> LENGTH: 71
<212> TYPE: DNA
<213> ORGANISM: Bos taurus

<400> SEQUENCE: 7
cacagttctg tgcacccagg tgtcaacaac tccatmacac tcggcctaaa gcatcgcttt   60
gctggtgtct g                                                        71

<210> SEQ ID NO 8
<211> LENGTH: 71
<212> TYPE: DNA
<213> ORGANISM: Bos taurus

<400> SEQUENCE: 8
gtctattcct ggaactttcc ccacttcagg gaaccyagga gcaggatagc aaacccaccc   60
aatcattcca c                                                        71

<210> SEQ ID NO 9
<211> LENGTH: 71

```
<212> TYPE: DNA
<213> ORGANISM: Bos Taurus

<400> SEQUENCE: 9
agcacgagct cacagaaact gcgagaagga caccaygaac acacggagca aagtccagta    60
cctcttgact c                                                        71

<210> SEQ ID NO 10
<211> LENGTH: 71
<212> TYPE: DNA
<213> ORGANISM: Bos taurus

<400> SEQUENCE: 10
agacaaatgg aggcaacaga gcatagatgt gagacragtt ccaggcctga cgcagcacga    60
aggagaaact g                                                        71

<210> SEQ ID NO 11
<211> LENGTH: 71
<212> TYPE: DNA
<213> ORGANISM: Bos taurus

<400> SEQUENCE: 11
aggaagaatg gaatattaaa gcagcagatt agattrcagg taaaaccacc ttggccaggg    60
ggactacagc a                                                        71

<210> SEQ ID NO 12
<211> LENGTH: 71
<212> TYPE: DNA
<213> ORGANISM: Bos Taurus

<400> SEQUENCE: 12
atatagtaga gaaatataca tgtctcagac cacccytcct cctctgatgg gcccaggtac    60 atgaatttt t                                                         71

<210> SEQ ID NO 13
<211> LENGTH: 71
<212> TYPE: DNA
<213> ORGANISM: Bos Taurus

<400> SEQUENCE: 13
actgatctaa tctgacccat tggccttttt tttttwaatt gagcttgcat gagctgttaa    60
tgtattttga a                                                        71

<210> SEQ ID NO 14
<211> LENGTH: 71
<212> TYPE: DNA
<213> ORGANISM: Bos Tuarus

<400> SEQUENCE: 14
actcctactg agtcaactgt aaatactgtg tatctyagaa gttaattgtc agtaaaaaac    60
acatgagcac a                                                        71

<210> SEQ ID NO 15
<211> LENGTH: 71
<212> TYPE: DNA
<213> ORGANISM: bos taurus

<400> SEQUENCE: 15
taggacatga tacatgttgg gtaaagcaaa aggccrtgcc aaaattcata ttgttaaaaa    60
```

```
gaaacttgag g                                                          71

<210> SEQ ID NO 16
<211> LENGTH: 71
<212> TYPE: DNA
<213> ORGANISM: Bos taurus

<400> SEQUENCE: 16
gtgctcatcc aagggtgttc tgagcaggaa aggccrctgg tcaggcagcc cagaaggtga    60
gtttgcccat c                                                          71

<210> SEQ ID NO 17
<211> LENGTH: 71
<212> TYPE: DNA
<213> ORGANISM: Bos taurus

<400> SEQUENCE: 17
ctgacagaat acttgaatac aggcagagct tgcagrtttt gcatgcttgg ttccaaccac    60
cacaataaag t                                                          71

<210> SEQ ID NO 18
<211> LENGTH: 71
<212> TYPE: DNA
<213> ORGANISM: Bos taurus

<400> SEQUENCE: 18
tgctgctcaa tgttcccaaa ttgtgtgcca ccagarggcc tgattttgca gggaaaagag    60
aagtgggtcc c                                                          71

<210> SEQ ID NO 19
<211> LENGTH: 71
<212> TYPE: DNA
<213> ORGANISM: Bos taurus

<400> SEQUENCE: 19
agtgctggcc accgctggac aatcagcctg aggccrgagc ttggaggaac aaagtccaag    60
gaccgcaaac a                                                          71

<210> SEQ ID NO 20
<211> LENGTH: 71
<212> TYPE: DNA
<213> ORGANISM: bos taurus

<400> SEQUENCE: 20
ctcctggctg gggctgggtg gctgcaggga ggtgartctg gggccaaggt taaagcacct    60
gtagacattt c                                                          71

<210> SEQ ID NO 21
<211> LENGTH: 71
<212> TYPE: DNA
<213> ORGANISM: Bos taurus

<400> SEQUENCE: 21
cttccggtga ttagggtta taaaaatgcc atttayccag caaggatggt catgtgaatt    60
ggagactgat c                                                          71

<210> SEQ ID NO 22
<211> LENGTH: 71
<212> TYPE: DNA
<213> ORGANISM: bos taurus
```

<400> SEQUENCE: 22
agtaaatctc tcaaacaagt ttataaccgt ggcctscaca aaaggcatca aatctgggtc    60
tcgcatgaaa a                                                         71

<210> SEQ ID NO 23
<211> LENGTH: 71
<212> TYPE: DNA
<213> ORGANISM: bos taurus

<400> SEQUENCE: 23
ttcattctgg tctctgctta agtgtcatct ccccaragag gcctttttg gccaccctat    60 gtaaggagag t                                                         71

<210> SEQ ID NO 24
<211> LENGTH: 71
<212> TYPE: DNA
<213> ORGANISM: bos taurus

<400> SEQUENCE: 24
aggcatggct ccctccacat aaacacagag cctcayagca aggccagaac ctataggcaa    60
agggagttca a                                                         71

<210> SEQ ID NO 25
<211> LENGTH: 71
<212> TYPE: DNA
<213> ORGANISM: bos taurus

<400> SEQUENCE: 25
caccccctgc cagcctaagt ggctcctaac ccctcrgtgc atcacctata aggcctgcac    60
acaggcacaa a                                                         71

<210> SEQ ID NO 26
<211> LENGTH: 71
<212> TYPE: DNA
<213> ORGANISM: bos taurus

<400> SEQUENCE: 26
acaggagaag ggagagaaca ctggcaggca ctaacrtatc cactttatct acagtgctgt    60
agcttttagt t                                                         71

<210> SEQ ID NO 27
<211> LENGTH: 71
<212> TYPE: DNA
<213> ORGANISM: bos taurus

<400> SEQUENCE: 27
tcattttctt tgaaggtcaa tagggccact atcacrtaaa ataaaagtta cttggaaata    60
agttctgtaa t                                                         71

<210> SEQ ID NO 28
<211> LENGTH: 71
<212> TYPE: DNA
<213> ORGANISM: Bos taurus

<400> SEQUENCE: 28
attaataaac agatactttc ttttccattt caccakaagt cttttgtact gcgttttaaa    60
actagctttg t                                                         71

<210> SEQ ID NO 29
<211> LENGTH: 71
<212> TYPE: DNA
<213> ORGANISM: Bos Taurus

<400> SEQUENCE: 29
gagtggaggc aatagtggtg gcctcgctgg gaaatkagcc tgcttgctgg gtctatagca    60
ggatgccatt g    71

<210> SEQ ID NO 30
<211> LENGTH: 71
<212> TYPE: DNA
<213> ORGANISM: Bos taurus

<400> SEQUENCE: 30
cagccactca ggcctagccc tccctgcaag tgggtkgagc agatgagagc cccgaaggaa    60
agactgagca t    71

<210> SEQ ID NO 31
<211> LENGTH: 71
<212> TYPE: DNA
<213> ORGANISM: Bos taurus

<400> SEQUENCE: 31
cggccacgag gatgcggccg tgctcttggt agtccrcttg ggtgcgcagg tgcacgtgcg    60
cgaccacagc g    71

<210> SEQ ID NO 32
<211> LENGTH: 71
<212> TYPE: DNA
<213> ORGANISM: Bos taurus

<400> SEQUENCE: 32
tacagtgagg caccttcctc cactgtccgc gccagyacag gggcccagga cagcaagctg    60
accggctcag g    71

<210> SEQ ID NO 33
<211> LENGTH: 71
<212> TYPE: DNA
<213> ORGANISM: Bos taurus

<400> SEQUENCE: 33
cagccaggtg gacacagatc tatattcaga ccttgyccac tgaggcctct tgatacttag    60
caatatttca t    71

<210> SEQ ID NO 34
<211> LENGTH: 71
<212> TYPE: DNA
<213> ORGANISM: Bos taurus

<400> SEQUENCE: 34
ctggctgatc tcccacaagt gaggggggctt cacagkgtac aggaaccttt ctcctctcac    60
agcttccttc c    71

<210> SEQ ID NO 35
<211> LENGTH: 71
<212> TYPE: DNA
<213> ORGANISM: Bos taurus

<400> SEQUENCE: 35

```
acaatgtgaa cagtaccgca gtaggccttt gtcccrtgga aagctccctg taagggtgtg    60
aggccatcag t                                                          71

<210> SEQ ID NO 36
<211> LENGTH: 71
<212> TYPE: DNA
<213> ORGANISM: Bos taurus

<400> SEQUENCE: 36
gtatttagct acatttatct ttcccaggga aaattyctgc tccaaagatt ggataagtgc    60
catttttatg g                                                          71

<210> SEQ ID NO 37
<211> LENGTH: 71
<212> TYPE: DNA
<213> ORGANISM: Bos taurus

<400> SEQUENCE: 37
caatttatga agtgtgggcc atatcactac ttgtcmaaag gaaccctatg ttttaaaact    60
caaaggggtt a                                                          71

<210> SEQ ID NO 38
<211> LENGTH: 71
<212> TYPE: DNA
<213> ORGANISM: Bos Taurus

<400> SEQUENCE: 38
tcttggctct atcatagagc tctatttact tcttarccat cactctattc caagccacca    60
tcatctccac c                                                          71

<210> SEQ ID NO 39
<211> LENGTH: 71
<212> TYPE: DNA
<213> ORGANISM: Bos taurus

<400> SEQUENCE: 39
ccagagcagt cagttcaccc caggccagag gccacyggga gaccctgctg cgttgactca    60
ttacagcgaa a                                                          71

<210> SEQ ID NO 40
<211> LENGTH: 71
<212> TYPE: DNA
<213> ORGANISM: Bos taurus

<400> SEQUENCE: 40
agggagatgg aggatagagg aaagtgtttt tggccraagg actagagtga ggcaagaccc    60
caatttaaga c                                                          71

<210> SEQ ID NO 41
<211> LENGTH: 71
<212> TYPE: DNA
<213> ORGANISM: Bos Taurus

<400> SEQUENCE: 41
agacccagaa agaatagaat ggctcttggg gatataraggt ggccatcaaa ttgaactcat    60
gagctctaaa c                                                          71

<210> SEQ ID NO 42
```

```
<211> LENGTH: 71
<212> TYPE: DNA
<213> ORGANISM: Bos Taurus

<400> SEQUENCE: 42
tgagccttag cccaggtccc acacacaggc ctgaargtct accacagtca actctgacac    60
aactgttagg a                                                         71

<210> SEQ ID NO 43
<211> LENGTH: 71
<212> TYPE: DNA
<213> ORGANISM: Bos Taurus

<400> SEQUENCE: 43
tacaggttgg tctggataca agagttggcc cacaayagga attgaagaag cagagaatag    60
aagaaggcag a                                                         71

<210> SEQ ID NO 44
<211> LENGTH: 71
<212> TYPE: DNA
<213> ORGANISM: Bos taurus

<400> SEQUENCE: 44
tggcggcgga gggactggag gggcacacgg tggccrcgtt accgccgtgt ctgctcccgg    60
aggattaact c                                                         71

<210> SEQ ID NO 45
<211> LENGTH: 71
<212> TYPE: DNA
<213> ORGANISM: Bos Tuarus

<400> SEQUENCE: 45
ggtgcgcgca cgcgacacgg cgtcgcccat ggcgycttc atgtggccgc tgcactggtc     60
catgtggctg g                                                         71

<210> SEQ ID NO 46
<211> LENGTH: 71
<212> TYPE: DNA
<213> ORGANISM: bos taurus

<400> SEQUENCE: 46
cacagagctc acacagcacg gcctgttggc acggargcac tgctcggttc tgctcctgac    60
acttaaggca t                                                         71

<210> SEQ ID NO 47
<211> LENGTH: 71
<212> TYPE: DNA
<213> ORGANISM: Bos taurus

<400> SEQUENCE: 47
cacatttatt tgggtctgca tgatatgtct caaatrtctc cagacttggc ctttattaag    60
caagttctac a                                                         71

<210> SEQ ID NO 48
<211> LENGTH: 71
<212> TYPE: DNA
<213> ORGANISM: Bos taurus

<400> SEQUENCE: 48
aggaaatgac tctcccaggc ctccctgaag cttctratct ggcaaggaag accctttct    60
```
gtcacttcca a                                                           71

<210> SEQ ID NO 49
<211> LENGTH: 71
<212> TYPE: DNA
<213> ORGANISM: Bos Taurus

<400> SEQUENCE: 49
ttcctagaga ccctgctgtg ggtggcccag gaaacktcca gagaagcagg aataactcta    60
agtgtaagtc a                                                           71

<210> SEQ ID NO 50
<211> LENGTH: 71
<212> TYPE: DNA
<213> ORGANISM: Bos taurus

<400> SEQUENCE: 50
tggtgagtgt ggggtgggaa tctagctggt gggggyagct cccagattcg gggggccagt    60
tgtgtctgct g                                                           71

<210> SEQ ID NO 51
<211> LENGTH: 71
<212> TYPE: DNA
<213> ORGANISM: Bos Tuarus

<400> SEQUENCE: 51
atttcttaat aaaccacatg tactttcgcc aaccaktgaa atggtcccct tgttccctta    60
gttcaggcta t                                                           71

<210> SEQ ID NO 52
<211> LENGTH: 71
<212> TYPE: DNA
<213> ORGANISM: Bos taurus

<400> SEQUENCE: 52
ttctcctacc cacatccaaa tctctggcct gctccrggtc ccccagcaga cacatcctta    60
ctgtggagac a                                                           71

<210> SEQ ID NO 53
<211> LENGTH: 71
<212> TYPE: DNA
<213> ORGANISM: Bos taurus

<400> SEQUENCE: 53
agcctactac taccaattcg aggcccaaag caaacrgagt cccagtatct taagtttgga    60
aaatgtgtca c                                                           71

<210> SEQ ID NO 54
<211> LENGTH: 71
<212> TYPE: DNA
<213> ORGANISM: Bos taurus

<400> SEQUENCE: 54
cacctgcccc ccaccccctcg accccggcct ttcctmttcc ttctgatgat gattccagtg    60
acatttccag c                                                           71

<210> SEQ ID NO 55
<211> LENGTH: 71
<212> TYPE: DNA

<213> ORGANISM: Bos taurus

<400> SEQUENCE: 55
ttgggctcag gagccctact ggtgggccca gggackctta attcagcaga agctattcaa    60
cccttgtcaa t    71

<210> SEQ ID NO 56
<211> LENGTH: 71
<212> TYPE: DNA
<213> ORGANISM: Bos taurus

<400> SEQUENCE: 56
atgggctcat gtatagatga gaggtctcat ttgttyctaa atcctcagga aggcctgcct    60
gctgagaact t    71

<210> SEQ ID NO 57
<211> LENGTH: 71
<212> TYPE: DNA
<213> ORGANISM: Bos taurus

<400> SEQUENCE: 57
ccagatatga gagccagatg gaggctctcg cctggragct tggccatgtt caggggatgc    60
tccagcatcg t    71

<210> SEQ ID NO 58
<211> LENGTH: 71
<212> TYPE: DNA
<213> ORGANISM: Bos taurus

<400> SEQUENCE: 58
ccttcacctg tgttttttg ccttttttca ggatcraacc tccaagctct catagacagc    60
actagggagc c    71

<210> SEQ ID NO 59
<211> LENGTH: 71
<212> TYPE: DNA
<213> ORGANISM: Bos taurus

<400> SEQUENCE: 59
acagttgagc attcatgagt tacaagttcc caaagyccca caagctacgg gcctgttctc    60
tagacgtact a    71

<210> SEQ ID NO 60
<211> LENGTH: 71
<212> TYPE: DNA
<213> ORGANISM: Bos taurus

<400> SEQUENCE: 60
tgccattaac agtcatgttt ttaacatttt ctttcmtgag aacacacgct cagagatttt    60
cagttctagt t    71

<210> SEQ ID NO 61
<211> LENGTH: 71
<212> TYPE: DNA
<213> ORGANISM: Bos taurus

<400> SEQUENCE: 61
aatccaattt tctgttgatg ggctgggctg agttcrcgcc ctgttgtttg gatgaggcca    60
aactgttgac c    71

<210> SEQ ID NO 62
<211> LENGTH: 71
<212> TYPE: DNA
<213> ORGANISM: Bos taurus

<400> SEQUENCE: 62
taaaatctct gcaagcaaaa aagagaagaa aggatkgggg agagagcagt tcaggcagaa    60
gaagttgaaa t                                                        71

<210> SEQ ID NO 63
<211> LENGTH: 71
<212> TYPE: DNA
<213> ORGANISM: Bos taurus

<400> SEQUENCE: 63 gggacccat cctgccctga cctgagagca gcctcrggtg gagccctcag tggccaaaca    60
gaaccctgct c                                                        71

<210> SEQ ID NO 64
<211> LENGTH: 71
<212> TYPE: DNA
<213> ORGANISM: Bos taurus

<400> SEQUENCE: 64
tattagattt taattaattg gtttctatcc tacctkattt tgattggtgt ttgatttgtt    60
ttacaagtta a                                                        71

<210> SEQ ID NO 65
<211> LENGTH: 71
<212> TYPE: DNA
<213> ORGANISM: Bos taurus

<400> SEQUENCE: 65
tccttggggc tggcccttgc cagggtcaat tcaccrgtcc tttctcatct cgtacctact    60
ttccacaccg g                                                        71

<210> SEQ ID NO 66
<211> LENGTH: 71
<212> TYPE: DNA
<213> ORGANISM: Bos taurus

<400> SEQUENCE: 66
attcttccat ttttatttct agcatgtgta aactakatcc taaatttcct gaggctacag    60
ttcccatact a                                                        71

<210> SEQ ID NO 67
<211> LENGTH: 71
<212> TYPE: DNA
<213> ORGANISM: Bos taurus

<400> SEQUENCE: 67
ccttctggta aaggtgaaac ctgagccacc tggccrgagt atccaggcac tgctaggtga    60
ggctaccaag g                                                        71

<210> SEQ ID NO 68
<211> LENGTH: 71
<212> TYPE: DNA
<213> ORGANISM: Bos taurus

<400> SEQUENCE: 68
tgggattttt gttgcttaga aagaggccta aatccrggga atgctctctc cctctagccc    60
ttctctccct c    71

<210> SEQ ID NO 69
<211> LENGTH: 71
<212> TYPE: DNA
<213> ORGANISM: Bos taurus

<400> SEQUENCE: 69
aagggagggg caggtgccac ctcctaaggc ctcacygctg agatcactcc aaggggtgt    60 tcaggtgtgg t    71

<210> SEQ ID NO 70
<211> LENGTH: 71
<212> TYPE: DNA
<213> ORGANISM: Bos taurus

<400> SEQUENCE: 70
tttctaatat ctcttcattg caggagtccc tggtcraggg ctggttttga ttgccaatgt    60
cataatctaa a    71

<210> SEQ ID NO 71
<211> LENGTH: 71
<212> TYPE: DNA
<213> ORGANISM: Bos taurus

<400> SEQUENCE: 71
atggcttagg ccaaattagg ttctcttatg tcaaayttgc tggcatatta ggttctcaat    60
atgccagaaa a    71

<210> SEQ ID NO 72
<211> LENGTH: 71
<212> TYPE: DNA
<213> ORGANISM: Bos taurus

<400> SEQUENCE: 72
cctgtccttt gctagttcat caaccatgac aaacaktgta tattgatttg gggcttcgta    60
gataactgaa g    71

<210> SEQ ID NO 73
<211> LENGTH: 71
<212> TYPE: DNA
<213> ORGANISM: Bos taurus

<400> SEQUENCE: 73
ggcagcaagt ggccaggctc aagtcttgga aatccyacca ccatgctctg ctgtgtgtgc    60
taagtcactt c    71

<210> SEQ ID NO 74
<211> LENGTH: 71
<212> TYPE: DNA
<213> ORGANISM: Bos taurus

<400> SEQUENCE: 74
caagtcaggg gcccccagcc gctgggatct aatgcrtgat gacctgacgt gaagctgagg    60
taacaataac a    71

```
<210> SEQ ID NO 75
<211> LENGTH: 71
<212> TYPE: DNA
<213> ORGANISM: Bos taurus

<400> SEQUENCE: 75
tgcagcccag tccctaacag gcaaggacca gtaccrgtct atggcccggg gtttggggag      60 accccctgcac t                                                          71

<210> SEQ ID NO 76
<211> LENGTH: 71
<212> TYPE: DNA
<213> ORGANISM: Bos taurus

<400> SEQUENCE: 76
tctcagtcaa ccagaaagaa catccaacag ctatayggta aggattagtt aggagacctt      60
agaaatcaaa a                                                           71

<210> SEQ ID NO 77
<211> LENGTH: 71
<212> TYPE: DNA
<213> ORGANISM: Bos taurus

<400> SEQUENCE: 77
catagtaaaa tgtcactaca gttaaatgtg ttgaamaggt ggtgaaggcc ttttttcttc      60
catcttttga a                                                           71

<210> SEQ ID NO 78
<211> LENGTH: 71
<212> TYPE: DNA
<213> ORGANISM: Bos taurus

<400> SEQUENCE: 78
ctgccatgtt catatatatg cggcctgtgt ctgacmgatc ccctacccag gacaagatgg      60
tatcagcctt c                                                           71

<210> SEQ ID NO 79
<211> LENGTH: 71
<212> TYPE: DNA
<213> ORGANISM: Bos taurus

<400> SEQUENCE: 79
agtggatttc tcctgtagtg aaataagcct tcccckgagt aagtaggctg gaacacactt      60
cccagctgat g                                                           71

<210> SEQ ID NO 80
<211> LENGTH: 71
<212> TYPE: DNA
<213> ORGANISM: Bos taurus

<400> SEQUENCE: 80
atgagtgcag aaacatctga atcttgttct gtaagygggc cagtctctct gttcatgttt      60
taaccaaatt g                                                           71

<210> SEQ ID NO 81
<211> LENGTH: 71
<212> TYPE: DNA
<213> ORGANISM: Bos taurus

<400> SEQUENCE: 81
```

```
atgaataata aaattttagt aaacgcggtg ctttcyctat ttcatatatt gggcaattgc    60
atataaccat t                                                        71

<210> SEQ ID NO 82
<211> LENGTH: 71
<212> TYPE: DNA
<213> ORGANISM: Bos taurus

<400> SEQUENCE: 82
attcaatgta tttcgcaaat ctcctgactt ttctgyattt tcaaatttaa tgattacaac    60
tgtggttgaa a                                                        71

<210> SEQ ID NO 83
<211> LENGTH: 71
<212> TYPE: DNA
<213> ORGANISM: Bos taurus

<400> SEQUENCE: 83
gcaagagtac tggagtgggg tgccattgtc ttctcytgta ctaggccagg gttcttgaaa    60
aataatgcag a                                                        71

<210> SEQ ID NO 84
<211> LENGTH: 71
<212> TYPE: DNA
<213> ORGANISM: Bos taurus

<400> SEQUENCE: 84
aagccccgaa gaggaacatt aagttcagtg cagtcrctca gtcatacccg actctttgcg    60
aacccatgag c                                                        71

<210> SEQ ID NO 85
<211> LENGTH: 71
<212> TYPE: DNA
<213> ORGANISM: Bos taurus

<400> SEQUENCE: 85
gcagactcct tggtgcctgc cagatcttgg aggcgrcatg gtaatccttt gttttttgagt   60 ttgttcaaca t                                                        71

<210> SEQ ID NO 86
<211> LENGTH: 71
<212> TYPE: DNA
<213> ORGANISM: Bos taurus

<400> SEQUENCE: 86
tgtgtaggct gtacaaattg atttctgtcc aaagarcaga ggatggaaag gtgggcggaa    60
agtaacttta c                                                        71

<210> SEQ ID NO 87
<211> LENGTH: 71
<212> TYPE: DNA
<213> ORGANISM: Bos taurus

<400> SEQUENCE: 87
aacccattac acttgaatat ctgattcttg ccaatrcata atttaaagtc ttcacttcaa    60
aataatttgg t                                                        71

<210> SEQ ID NO 88
<211> LENGTH: 71
```

```
<212> TYPE: DNA
<213> ORGANISM: Bos taurus

<400> SEQUENCE: 88
ctaactttat tgactttaaa ggatttccat catagygtgt aattttgcaa aatttgttgc    60
atatttctgt t                                                         71

<210> SEQ ID NO 89
<211> LENGTH: 71
<212> TYPE: DNA
<213> ORGANISM: Bos taurus

<400> SEQUENCE: 89
ccagttccat ggagctcttg atcttcagcc tgtccratgc ctccttttgt ggcacaccac    60
ccaggtcttc t                                                         71

<210> SEQ ID NO 90
<211> LENGTH: 71
<212> TYPE: DNA
<213> ORGANISM: Bos taurus

<400> SEQUENCE: 90
cacttgtaaa atgccatttt tttctataga gatgtmtgat ttttcagact ttatatattc    60
tggatatgag t                                                         71

<210> SEQ ID NO 91
<211> LENGTH: 71
<212> TYPE: DNA
<213> ORGANISM: Bos taurus

<400> SEQUENCE: 91
cctaggtcga tgtccgtgaa gccctcagct gtgatrgcat cagccgtgtt cttgtcaatg    60
ttctccagac a                                                         71

<210> SEQ ID NO 92
<211> LENGTH: 71
<212> TYPE: DNA
<213> ORGANISM: Bos taurus

<400> SEQUENCE: 92
caagagacag gatagtaaat aaagggcaga ctgtgrcatt taaatctttt caaaaaagat    60
gtcatcagct c                                                         71

<210> SEQ ID NO 93
<211> LENGTH: 71
<212> TYPE: DNA
<213> ORGANISM: Bos taurus

<400> SEQUENCE: 93
agcctctcct tcctggacct ctgtttcacc accacractg taccccaaat gctgttcaac    60
ttaggcggac c                                                         71

<210> SEQ ID NO 94
<211> LENGTH: 71
<212> TYPE: DNA
<213> ORGANISM: Bos taurus

<400> SEQUENCE: 94
aggctgaggg gtgcccagat ggagaactga atgaargcag tcaagtggta taaagttcca    60
```
gttacaagat a                                                           71

<210> SEQ ID NO 95
<211> LENGTH: 71
<212> TYPE: DNA
<213> ORGANISM: Bos taurus

<400> SEQUENCE: 95
actttcattt attgcagaat ttttattatt gctgtrtccc atgaaagtga attgagcaag      60
gagtaatgag a                                                           71

<210> SEQ ID NO 96
<211> LENGTH: 71
<212> TYPE: DNA
<213> ORGANISM: Bos taurus

<400> SEQUENCE: 96
tgccctggga tgatgggcaa ccactggcca cttacraggc cctcacagac tgtccttatc      60
agcagcagta c                                                           71

<210> SEQ ID NO 97
<211> LENGTH: 71
<212> TYPE: DNA
<213> ORGANISM: Bos taurus

<400> SEQUENCE: 97
tttttttaag atgtctctgc ttttgtagtt gttagyctgt tctgctgtgt gaggtttaga      60
tgaaatgaga g                                                           71

<210> SEQ ID NO 98
<211> LENGTH: 71
<212> TYPE: DNA
<213> ORGANISM: Bos taurus

<400> SEQUENCE: 98
accagggaag tcctgtacat tcttaaatag ctttgsaaga tggggattct gtgatgcttg      60
gggtatgaaa t                                                           71

<210> SEQ ID NO 99
<211> LENGTH: 71
<212> TYPE: DNA
<213> ORGANISM: Bos taurus

<400> SEQUENCE: 99
cacaatgaag cttgactacc caggccagta agttcktgtg ttatcagttg gcactcatta      60
tccctggaat g                                                           71

<210> SEQ ID NO 100
<211> LENGTH: 71
<212> TYPE: DNA
<213> ORGANISM: Bos taurus

<400> SEQUENCE: 100
ttaactctag atctgagatt ctgtctcttg gtttcrccat gattcctgga tttaattcga      60
gtacaaattt a                                                           71

<210> SEQ ID NO 101
<211> LENGTH: 71
<212> TYPE: DNA
<213> ORGANISM: Bos taurus

<400> SEQUENCE: 101
tgctatgggc ataagccagg aacgagcagc acagarttag ggaggggggcc tctgggtag        60 tggtcagagg t                                                             71

<210> SEQ ID NO 102
<211> LENGTH: 71
<212> TYPE: DNA
<213> ORGANISM: Bos taurus

<400> SEQUENCE: 102
taaatgcttt acttactgta atacattgta gtagcraaga gcactgtttt tgaagctaca        60
aacctaggtt t                                                             71

<210> SEQ ID NO 103
<211> LENGTH: 71
<212> TYPE: DNA
<213> ORGANISM: Bos taurus

<400> SEQUENCE: 103
ctggatagtg acagactagt atcaggcatt cttacrtatg tctagccagg aggggatttt       60
tttttttttt t                                                             71

<210> SEQ ID NO 104
<211> LENGTH: 71
<212> TYPE: DNA
<213> ORGANISM: Bos taurus

<400> SEQUENCE: 104
aacatggggt gaattaataa atttgcttct gaaaaygccg agtttaacat aatgcaagga        60
cattgctata g                                                             71

<210> SEQ ID NO 105
<211> LENGTH: 71
<212> TYPE: DNA
<213> ORGANISM: Bos taurus

<400> SEQUENCE: 105
gccagtgagc tgcactcttg ctcttagatt tctgcygagt cctattatca ctctgaagga        60
actggctgct t                                                             71

<210> SEQ ID NO 106
<211> LENGTH: 71
<212> TYPE: DNA
<213> ORGANISM: Bos taurus

<400> SEQUENCE: 106
gatgtctcaa agcatgggtg atgataactt tagtakttta gatgctaatg aagcagaaat        60
cgaaccagaa a                                                             71

<210> SEQ ID NO 107
<211> LENGTH: 71
<212> TYPE: DNA
<213> ORGANISM: Bos taurus

<400> SEQUENCE: 107
cattatggtg aagtattagg ggataaataa atagamaaga taagtaggct gcccagactg        60
ggtgagttag a                                                             71

<210> SEQ ID NO 108
<211> LENGTH: 71
<212> TYPE: DNA
<213> ORGANISM: Bos taurus

<400> SEQUENCE: 108
cagcacacca aattcaggtg atgacagctg tgcccrgtca tcagctgtcc ttcttggagg    60
gaccatgaga a    71

<210> SEQ ID NO 109
<211> LENGTH: 71
<212> TYPE: DNA
<213> ORGANISM: Bos taurus

<400> SEQUENCE: 109
gtgttgcctc tatagcaact tgaaaaggtt ataatygtat taccaagaaa aagaaatcag    60
acacatttag g    71

<210> SEQ ID NO 110
<211> LENGTH: 71
<212> TYPE: DNA
<213> ORGANISM: Bos taurus

<400> SEQUENCE: 110
tataaacata tgtacttcat ttataaagaa ttgcaytggt gaaggaaaaa atctctgact    60
agccttgata t    71

<210> SEQ ID NO 111
<211> LENGTH: 71
<212> TYPE: DNA
<213> ORGANISM: Bos taurus

<400> SEQUENCE: 111
ctcattatga tgaaaaagcc actcaaagat tcgcayttct ctacttcctt ccggattagg    60
ttcattatag a    71

<210> SEQ ID NO 112
<211> LENGTH: 71
<212> TYPE: DNA
<213> ORGANISM: Bos taurus

<400> SEQUENCE: 112
actgttttta agggaaaaac aatgcatgcc ctcggktatg gagatgttga gtttgaggta    60
cacataagag a    71

<210> SEQ ID NO 113
<211> LENGTH: 71
<212> TYPE: DNA
<213> ORGANISM: Bos taurus

<400> SEQUENCE: 113
ctaatatttt attagtattg atttcccatt tgcctrgtag cctagtatta gtgaattcac    60
tgaactatta c    71

<210> SEQ ID NO 114
<211> LENGTH: 71
<212> TYPE: DNA
<213> ORGANISM: Bos taurus

<400> SEQUENCE: 114

```
cctgcttgat attcatcagc ttcacacaga tcttaygaac agcatcgttc tcatgaacaa    60
ggagggcgtc t                                                         71

<210> SEQ ID NO 115
<211> LENGTH: 71
<212> TYPE: DNA
<213> ORGANISM: Bos taurus

<400> SEQUENCE: 115
gtgtgtatag gtattcaaag ctgaaacagg agagawactt ctagaaatca aggctcatga    60
ggatgaagtg c                                                         71

<210> SEQ ID NO 116
<211> LENGTH: 71
<212> TYPE: DNA
<213> ORGANISM: Bos taurus

<400> SEQUENCE: 116
tggctgtagg aattgtcatc tcgtttccac ataccrtggg tgaaggttgg gcatgtgctt    60
tttcagtttt a                                                         71

<210> SEQ ID NO 117
<211> LENGTH: 71
<212> TYPE: DNA
<213> ORGANISM: Bos taurus

<400> SEQUENCE: 117
gactttggat ctattttttc tactcttttg cctggygcta atgctatgct tgcaccacca    60
gaagggcaga c                                                         71

<210> SEQ ID NO 118
<211> LENGTH: 71
<212> TYPE: DNA
<213> ORGANISM: Bos taurus

<400> SEQUENCE: 118
tcagaatttg agaatgcctt tacttccaag gttcaygatc tttcaactac acaactgttt    60
ctaaaatatt a                                                         71

<210> SEQ ID NO 119
<211> LENGTH: 71
<212> TYPE: DNA
<213> ORGANISM: Bos taurus

<400> SEQUENCE: 119
ttaacctagg atatgagggt acaggcttgg atatargatg catatttcta agtcaagact    60
aacagatagg g                                                         71

<210> SEQ ID NO 120
<211> LENGTH: 71
<212> TYPE: DNA
<213> ORGANISM: Bos taurus

<400> SEQUENCE: 120
agatactgag aataaatatt taatggaaat taaagraact caaaactgtg agaattctct    60
attaacaact t                                                         71

<210> SEQ ID NO 121
```

```
<211> LENGTH: 71
<212> TYPE: DNA
<213> ORGANISM: Bos taurus

<400> SEQUENCE: 121
gtcttatctg caaattacta aaaataatca gctctragaa gtgaccttgg atgaagcagt       60
attaaattgg c                                                            71

<210> SEQ ID NO 122
<211> LENGTH: 71
<212> TYPE: DNA
<213> ORGANISM: Bos taurus

<400> SEQUENCE: 122
ccttacctga aaattaggag taaaatattt aataakatat catcaataaa agacaatatc       60
gagtgcaata c                                                            71

<210> SEQ ID NO 123
<211> LENGTH: 71
<212> TYPE: DNA
<213> ORGANISM: Bos taurus

<400> SEQUENCE: 123
accaatggcc agtctgtgat gctgaactca gtaagyagaa tacatgagcc tgggaaacaa       60
gatgtaaaaa t                                                            71

<210> SEQ ID NO 124
<211> LENGTH: 71
<212> TYPE: DNA
<213> ORGANISM: Bos taurus

<400> SEQUENCE: 124
tatgtttatt gtttctctct aagcagtcca tgttayctcc ccaaagcgat tttccttttca      60 ttgcagatat g                                                            71

<210> SEQ ID NO 125
<211> LENGTH: 71
<212> TYPE: DNA
<213> ORGANISM: Bos taurus

<400> SEQUENCE: 125
tcttctcctc aactccctat caagcttttg gctggrgttt agctcccaga tgttagcctc       60
cactaactgg c                                                            71

<210> SEQ ID NO 126
<211> LENGTH: 71
<212> TYPE: DNA
<213> ORGANISM: Bos taurus

<400> SEQUENCE: 126
acagtcattc cagacaatgc attcttcagt gatgaygcag tcttgatatt atcaaaagaa       60
atgtttattt c                                                            71

<210> SEQ ID NO 127
<211> LENGTH: 71
<212> TYPE: DNA
<213> ORGANISM: Bos taurus

<400> SEQUENCE: 127
acttttacat aacatgcctg cagaatagaa gcaggrattt ttttttttct gggagattat      60
```
gaattctcat a                                                          71

<210> SEQ ID NO 128
<211> LENGTH: 71
<212> TYPE: DNA
<213> ORGANISM: Bos taurus

<400> SEQUENCE: 128
gcagagagaa agtcgggcct cagcagacag catgtrgagt ctggttcccg ggagcagcca    60
agacccagaa g                                                          71

<210> SEQ ID NO 129
<211> LENGTH: 71
<212> TYPE: DNA
<213> ORGANISM: Bos taurus

<400> SEQUENCE: 129
agtcagctct ttgcatcagg tggccaaagt ataatycata ttaattaatg gtatataagg    60
gcatgtgagt t                                                          71

<210> SEQ ID NO 130
<211> LENGTH: 71
<212> TYPE: DNA
<213> ORGANISM: Bos taurus

<400> SEQUENCE: 130
gaatagaatc aggagatttt gaaggaggag tgcatyacag tattaagtgt ggctaaaaag    60
ataagaagga t                                                          71

<210> SEQ ID NO 131
<211> LENGTH: 71
<212> TYPE: DNA
<213> ORGANISM: Bos taurus

<400> SEQUENCE: 131
catttgtgta tattaccagt gcatatatta gcagcrtttt ctaggcttca ggaaatgctt    60
ctaaaattac t                                                          71

<210> SEQ ID NO 132
<211> LENGTH: 71
<212> TYPE: DNA
<213> ORGANISM: Bos taurus

<400> SEQUENCE: 132
tacattgcgt gtgtgtgtgt gcattttaga cacacrttta aagacaaaa tgtcaaagaa     60 gagcctcgag a                                                          71

<210> SEQ ID NO 133
<211> LENGTH: 71
<212> TYPE: DNA
<213> ORGANISM: Bos taurus

<400> SEQUENCE: 133
taaagtttta gtagaagaac attaggatgt gtataraaaa ggaagaatgg gcagtcatat    60
caagaaagta t                                                          71

<210> SEQ ID NO 134
<211> LENGTH: 71
<212> TYPE: DNA

<213> ORGANISM: Bos taurus

<400> SEQUENCE: 134
aggtgggaag gaggcactgc aaatagaatt cctggrgctt tcaatcaggc cagagagagg    60
acattgtggg g                                                        71

<210> SEQ ID NO 135
<211> LENGTH: 71
<212> TYPE: DNA
<213> ORGANISM: Bos taurus

<400> SEQUENCE: 135
gactagagga catgggcagc gttctggaca tcaggyagtg accatgggct ccctgccctg    60
atggccggca c                                                        71

<210> SEQ ID NO 136
<211> LENGTH: 71
<212> TYPE: DNA
<213> ORGANISM: Bos taurus

<400> SEQUENCE: 136
tctaacttga aacttataac ggcatgtttt tctttkgggg aagaaaaaa gcctaaaatc    60 atgactgaat c                                                        71

<210> SEQ ID NO 137
<211> LENGTH: 71
<212> TYPE: DNA
<213> ORGANISM: Bos taurus

<400> SEQUENCE: 137
gaaatccaca aatccacagt gagttttaaa aactgrgcaa ataaatgggg taaagtagaa    60
aagtcttcct t                                                        71

<210> SEQ ID NO 138
<211> LENGTH: 71
<212> TYPE: DNA
<213> ORGANISM: Bos taurus

<400> SEQUENCE: 138
ggatgtacga aagtcaagga tgatgttagt gcttaygatg agtgtgtcta actagaggat    60
ttatttctca c                                                        71

<210> SEQ ID NO 139
<211> LENGTH: 71
<212> TYPE: DNA
<213> ORGANISM: Bos taurus

<400> SEQUENCE: 139
aggaagaaac cccagacaag taaacagagg aaggtrtcag aaaacaggat gatgtctaat    60
catgaatcgc a                                                        71

<210> SEQ ID NO 140
<211> LENGTH: 71
<212> TYPE: DNA
<213> ORGANISM: Bos taurus

<400> SEQUENCE: 140
ccagcagtat gaaatcagaa ttaaaggtct gaaatyccca tgccatgatg aatgtgttct    60
ttaactatta a                                                        71

<210> SEQ ID NO 141
<211> LENGTH: 71
<212> TYPE: DNA
<213> ORGANISM: Bos taurus

<400> SEQUENCE: 141
ggaccctacc aaccggtaaa tacctccagc ccctcrcctt tgtggtggca gacttgagat    60
ttgttgtccc g                                                        71

<210> SEQ ID NO 142
<211> LENGTH: 71
<212> TYPE: DNA
<213> ORGANISM: Bos taurus

<400> SEQUENCE: 142
agacttgacc tttatatatc tggttaatgt ctagaytgtt gattattccc tggggctagg    60
aagaactgga a                                                        71

<210> SEQ ID NO 143
<211> LENGTH: 71
<212> TYPE: DNA
<213> ORGANISM: Bos taurus

<400> SEQUENCE: 143
ggacataggg acaggggagg aggaccagac accaayaggt aatagtaact accctcactg    60
tttcatcaac c                                                        71

<210> SEQ ID NO 144
<211> LENGTH: 71
<212> TYPE: DNA
<213> ORGANISM: Bos taurus

<400> SEQUENCE: 144
gggctttcac acattgcaaa gaaaatcagt cacaayaaaa actgcctgat gagagactgt    60
tgcacacttt g                                                        71

<210> SEQ ID NO 145
<211> LENGTH: 71
<212> TYPE: DNA
<213> ORGANISM: Bos taurus

<400> SEQUENCE: 145
gagccagggc tccaggagag atagaaactg cacccygccc cccaactcct gactgaaggc    60
tggatcgccc t                                                        71

<210> SEQ ID NO 146
<211> LENGTH: 71
<212> TYPE: DNA
<213> ORGANISM: Bos taurus

<400> SEQUENCE: 146
ttctttcaaa tgaacattgt aaaaatatga actagktttc aacttaaatt gaaaacaaaa    60
tttaggaaca t                                                        71

<210> SEQ ID NO 147
<211> LENGTH: 71
<212> TYPE: DNA
<213> ORGANISM: Bos taurus

```
<400> SEQUENCE: 147
ttatctgttt tgctcatct taatataaaa atcttracag ttatggttcg agttcacctg    60
gatgagattt c                                                       71

<210> SEQ ID NO 148
<211> LENGTH: 71
<212> TYPE: DNA
<213> ORGANISM: Bos taurus

<400> SEQUENCE: 148
ttccataact taaaaggacc atatgttcat tgagarggaa ttactagaaa tgatgaacgt    60
aatttttctt c                                                       71

<210> SEQ ID NO 149
<211> LENGTH: 71
<212> TYPE: DNA
<213> ORGANISM: Bos taurus

<400> SEQUENCE: 149
gatattagct ggttttaaat gtattttta cctttrgtgg tcgttattaa attttttaaca   60 taaaattcaa a                                                       71

<210> SEQ ID NO 150
<211> LENGTH: 71
<212> TYPE: DNA
<213> ORGANISM: Bos taurus

<400> SEQUENCE: 150
ggagtgtatt ataatgattt ttctatacta tttgtrttct tagtcactca gtcatgtccg    60
actctttgca a                                                       71

<210> SEQ ID NO 151
<211> LENGTH: 71
<212> TYPE: DNA
<213> ORGANISM: Bos taurus

<400> SEQUENCE: 151
cccctctgac cttctcactc tccagtcaaa ccagaygtct tctccagcac gggtcccttc    60
acttatatca g                                                       71

<210> SEQ ID NO 152
<211> LENGTH: 71
<212> TYPE: DNA
<213> ORGANISM: Bos taurus

<400> SEQUENCE: 152
acctcaggga aataaaaggt gattgttatg gccctkcctg attccagcag ccctgggtca    60
gatgcttccc a                                                       71

<210> SEQ ID NO 153
<211> LENGTH: 71
<212> TYPE: DNA
<213> ORGANISM: Bos taurus

<400> SEQUENCE: 153
ataaagagtt ggacaggact gaagtgactg agcatrcaca cactcaatca gtatatattt    60
tgaattattt a                                                       71
```

```
<210> SEQ ID NO 154
<211> LENGTH: 71
<212> TYPE: DNA
<213> ORGANISM: Bos taurus

<400> SEQUENCE: 154
ttaccagcgt tgttaaacgc tgcctgtgtt tcattytgct ttgatgctat ttgaggtagc      60
atgccagcag a                                                          71

<210> SEQ ID NO 155
<211> LENGTH: 71
<212> TYPE: DNA
<213> ORGANISM: Bos taurus

<400> SEQUENCE: 155
taacgtcgct tttcctcagt ttctgtagct ctgaayaggg gataataaca atatcttcct      60
caacacttgt a                                                          71

<210> SEQ ID NO 156
<211> LENGTH: 71
<212> TYPE: DNA
<213> ORGANISM: Bos taurus

<400> SEQUENCE: 156
cctacaaaca ggcatgcttg ccatcaattg taaaaygtct atatccccca agcccaggat      60
tcctctccta t                                                          71

<210> SEQ ID NO 157
<211> LENGTH: 71
<212> TYPE: DNA
<213> ORGANISM: Bos taurus

<400> SEQUENCE: 157
ctttgatgcc attattacca tttggtgact ctgtgrtcag caaatggttt gtcaatttaa      60
agtctggaat c                                                          71

<210> SEQ ID NO 158
<211> LENGTH: 71
<212> TYPE: DNA
<213> ORGANISM: Bos taurus

<400> SEQUENCE: 158 atattttga cattagcaaa aactgcttta gaggtrgatt gctactaata tcatatattt       60
taatactgtc a                                                          71

<210> SEQ ID NO 159
<211> LENGTH: 71
<212> TYPE: DNA
<213> ORGANISM: Bos taurus

<400> SEQUENCE: 159
ggaagaaaag ttttttttt tctcttaatg gaaacratat agcctggacc ctgtaaaggt       60
gcacacaaat a                                                          71

<210> SEQ ID NO 160
<211> LENGTH: 71
<212> TYPE: DNA
<213> ORGANISM: Bos taurus

<400> SEQUENCE: 160
```

```
ctgcactgta agccagctgt catgaacata ctaaaytatg tcattgccta tcgcttttat    60
agcatctcct a                                                         71

<210> SEQ ID NO 161
<211> LENGTH: 71
<212> TYPE: DNA
<213> ORGANISM: Bos taurus

<400> SEQUENCE: 161
agacagtaaa ttaattataa ggtcatgtca acagaraagt aatgcacaag acaaacagct    60
ctttatgtaa a                                                         71

<210> SEQ ID NO 162
<211> LENGTH: 71
<212> TYPE: DNA
<213> ORGANISM: Bos taurus

<400> SEQUENCE: 162
gcaacatgcc acagaatgtg ttcatggagc tcacaratgg gcaggaaaaa aagatagact    60
agaaatgacc a                                                         71

<210> SEQ ID NO 163
<211> LENGTH: 71
<212> TYPE: DNA
<213> ORGANISM: Bos taurus

<400> SEQUENCE: 163
taaaagtgct aaaatttgta actactttcc aattayattt aaccccaggt atgtactatt    60
ttcatatttt a                                                         71

<210> SEQ ID NO 164
<211> LENGTH: 71
<212> TYPE: DNA
<213> ORGANISM: Bos taurus

<400> SEQUENCE: 164
tagttaacat tgactaaggg ttggaggcgg ccaatrgacc tcgagaacaa gtataagctt    60
gtacttctct g                                                         71

<210> SEQ ID NO 165
<211> LENGTH: 39
<212> TYPE: DNA
<213> ORGANISM: Bos taurus

<400> SEQUENCE: 165
cactttgctc atgggagtat atgtgtatgt gagtaygtc                           39

<210> SEQ ID NO 166
<211> LENGTH: 71
<212> TYPE: DNA
<213> ORGANISM: Bos taurus

<400> SEQUENCE: 166
catgtttagg taagaaaact gttaaaatgt attcaygatg ccacttccct ttacttggtg    60
cagtttgccc a                                                         71

<210> SEQ ID NO 167
<211> LENGTH: 71
<212> TYPE: DNA
<213> ORGANISM: Bos taurus
```

```
<400> SEQUENCE: 167
gaagcagagg tgggtgaggg gtctaaacca ggagakgaac tagaccttca gacctgaagg    60
ttatctgatt c                                                        71

<210> SEQ ID NO 168
<211> LENGTH: 71
<212> TYPE: DNA
<213> ORGANISM: Bos taurus

<400> SEQUENCE: 168
tttggagaat tctgtgcctt ttcatactct cctctrctct tcttttcctc acactcgact    60
ttgttgcttc t                                                        71

<210> SEQ ID NO 169
<211> LENGTH: 71
<212> TYPE: DNA
<213> ORGANISM: Bos taurus

<400> SEQUENCE: 169
agaccagtgg accctaacac aaggacagag ttcatyggat atggccacag ggtccagccc    60
atgaggctgc c                                                        71

<210> SEQ ID NO 170
<211> LENGTH: 71
<212> TYPE: DNA
<213> ORGANISM: Bos taurus

<400> SEQUENCE: 170
caagggaagg agagcacttt tatggaagga agaggraatt gtgagggctg cagtccacaa    60
agagcccttg g                                                        71

<210> SEQ ID NO 171
<211> LENGTH: 71
<212> TYPE: DNA
<213> ORGANISM: Bos taurus

<400> SEQUENCE: 171 cccccctgggt gcctagggct gatgggtctg acccayggat ggaacgcctt gaatccagag    60
ccagttgcca g                                                        71

<210> SEQ ID NO 172
<211> LENGTH: 71
<212> TYPE: DNA
<213> ORGANISM: Bos taurus

<400> SEQUENCE: 172
aactttgtat ctacagaaag tactccttga tccccytcat ctctttggga ctcactccag    60
tgatgctgac t                                                        71

<210> SEQ ID NO 173
<211> LENGTH: 71
<212> TYPE: DNA
<213> ORGANISM: Bos taurus

<400> SEQUENCE: 173
gatgttcttt gcaactgttg tacctggttg gtaggraatc atataaaggt gtgctcctgc    60
aatcacttct c                                                        71
```

```
<210> SEQ ID NO 174
<211> LENGTH: 71
<212> TYPE: DNA
<213> ORGANISM: Bos taurus

<400> SEQUENCE: 174
ctatttgaca cagtggcatg tagactaggc agtcaracaa tgttgtctgt ccctctgagt      60
tgggactcaa a                                                          71

<210> SEQ ID NO 175
<211> LENGTH: 71
<212> TYPE: DNA
<213> ORGANISM: Bos taurus

<400> SEQUENCE: 175
gatgcagacg tttcaggaag gaggcactgc acaaartgag atagaggtac agggccccag      60
gcccccagag t                                                          71

<210> SEQ ID NO 176
<211> LENGTH: 71
<212> TYPE: DNA
<213> ORGANISM: Bos taurus

<400> SEQUENCE: 176
aatgagggta attgcctttc atgttcctaa tatttktgat ttagaaaaaa aaatcacccc      60
atttatcatt c                                                          71

<210> SEQ ID NO 177
<211> LENGTH: 71
<212> TYPE: DNA
<213> ORGANISM: Bos taurus

<400> SEQUENCE: 177
ggtactttgg gttaacagac tattacattg atgacrtgca ttatttgcct ctgttgcact      60
gattaaaggg t                                                          71

<210> SEQ ID NO 178
<211> LENGTH: 71
<212> TYPE: DNA
<213> ORGANISM: Bos taurus

<400> SEQUENCE: 178
ggccatttgt cttgggccta atcttgttca cgcagygtgg gaggctccaa ctgatcccaa      60
atttccccaa a                                                          71

<210> SEQ ID NO 179
<211> LENGTH: 71
<212> TYPE: DNA
<213> ORGANISM: Bos taurus

<400> SEQUENCE: 179
aagagtaggg tacaagtttg gaaagggggc ttctgrggcc cctatggggt gagaaatacg      60
agtatgagag t                                                          71

<210> SEQ ID NO 180
<211> LENGTH: 71
<212> TYPE: DNA
<213> ORGANISM: Bos taurus

<400> SEQUENCE: 180
```

```
aaacattttc agaattgaat gtggtctatg ttcacyttttt cctctcattt ggggaacttt    60
cccacttccc a                                                         71
```

<210> SEQ ID NO 181
<211> LENGTH: 71
<212> TYPE: DNA
<213> ORGANISM: Bos taurus

<400> SEQUENCE: 181

```
ttcaggggag ttcatttgca ggacctggag gaagaygaga gtataggaag tcagaatgag    60
gcttgtgggg a                                                         71
```

<210> SEQ ID NO 182
<211> LENGTH: 71
<212> TYPE: DNA
<213> ORGANISM: Bos taurus

<400> SEQUENCE: 182

```
gtagaaactt gatgtttgca acttgatgtt ttggtraaaa gtatataccc atgaaatcat    60
catcactatc a                                                         71
```

<210> SEQ ID NO 183
<211> LENGTH: 71
<212> TYPE: DNA
<213> ORGANISM: Bos taurus

<400> SEQUENCE: 183

```
aaaagactgt gtacactcac ttgaatttgc tttccrttct gtaaaggag agaatacgtt     60 ctattgtttg t                                                         71
```

<210> SEQ ID NO 184
<211> LENGTH: 71
<212> TYPE: DNA
<213> ORGANISM: Bos taurus

<400> SEQUENCE: 184

```
aaccattctc tcatcaacgt aagatagatt aatagmttgc taaatgcaac aggatttaat    60
gtgagtaggc a                                                         71
```

<210> SEQ ID NO 185
<211> LENGTH: 71
<212> TYPE: DNA
<213> ORGANISM: Bos taurus

<400> SEQUENCE: 185

```
tccaccacct ggaggcccct ccagctgcta gtttartctt ggagagcatg atcttaaacc    60
cactagccta t                                                         71
```

<210> SEQ ID NO 186
<211> LENGTH: 71
<212> TYPE: DNA
<213> ORGANISM: Bos taurus

<400> SEQUENCE: 186

```
aatgaaatgt tattatggag aagaagttga aacagmagcc agaaacttta agcctggcca    60
ataccttaat a                                                         71
```

<210> SEQ ID NO 187

```
<211> LENGTH: 71
<212> TYPE: DNA
<213> ORGANISM: Bos taurus

<400> SEQUENCE: 187
ttccagtact acagtttaaa agaacgaatt cttccrcgtt cagccttctt taggggccaa    60
tactcacgtc a                                                         71

<210> SEQ ID NO 188
<211> LENGTH: 71
<212> TYPE: DNA
<213> ORGANISM: Bos taurus

<400> SEQUENCE: 188
cccactttcc gaatcccatg ttccagcatc cagccycctt cacaccagca gaaacagatt    60
caggctgggt g                                                         71

<210> SEQ ID NO 189
<211> LENGTH: 71
<212> TYPE: DNA
<213> ORGANISM: Bos taurus

<400> SEQUENCE: 189
tgagtgtctc cttctgacct tcatgtcgta tgaccrattt gtggctattt gtaatcccct    60
gcaatacaca g                                                         71

<210> SEQ ID NO 190
<211> LENGTH: 71
<212> TYPE: DNA
<213> ORGANISM: Bos taurus

<400> SEQUENCE: 190
gatcttttgc ttatttattc attatattct ttatgmaata gttatctgaa ctcactgtca    60
ttaatctgaa c                                                         71

<210> SEQ ID NO 191
<211> LENGTH: 71
<212> TYPE: DNA
<213> ORGANISM: Bos taurus

<400> SEQUENCE: 191
ttgtattgct atctctccat aataattcaa ctttaycat cacaaaggag gaaacagagg     60
gaattttctc a                                                         71

<210> SEQ ID NO 192
<211> LENGTH: 71
<212> TYPE: DNA
<213> ORGANISM: Bos taurus

<400> SEQUENCE: 192
ggatgcccag aggcccatcc aactctgata tttttrgatc ctgcagtcat cactttcct    60 gctgtgtatc a                                                         71

<210> SEQ ID NO 193
<211> LENGTH: 71
<212> TYPE: DNA
<213> ORGANISM: Bos taurus

<400> SEQUENCE: 193
gtctcctgct gggcctggga gggggcgtgg ggaagracca tcaggagact gagctgcaaa    60
```
agacccctgg c                                                           71

<210> SEQ ID NO 194
<211> LENGTH: 71
<212> TYPE: DNA
<213> ORGANISM: Bos taurus

<400> SEQUENCE: 194
aataaggcag aagccctaat aattttgaaa caacarcagc aatcactgtt gcttcctctg      60
tggcaagcta t                                                           71

<210> SEQ ID NO 195
<211> LENGTH: 71
<212> TYPE: DNA
<213> ORGANISM: Bos taurus

<400> SEQUENCE: 195
aaatccaaaa aaaaggggg aggattgtaa aagtaytagt taaaaataaa gatgaattat       60
ttcatctgct c                                                           71

<210> SEQ ID NO 196
<211> LENGTH: 71
<212> TYPE: DNA
<213> ORGANISM: Bos taurus

<400> SEQUENCE: 196
gttgagtcgg acatagctgc ccttggatcc tagccyggcc cctgggcaca tggaaccgtg      60
gtgtcctggt c                                                           71

<210> SEQ ID NO 197
<211> LENGTH: 71
<212> TYPE: DNA
<213> ORGANISM: Bos taurus

<400> SEQUENCE: 197
ctcactggca gttggctgca ttcagttcct ggccgygtgg gtcttcctga attttcacct      60
tggcttctag c                                                           71

<210> SEQ ID NO 198
<211> LENGTH: 71
<212> TYPE: DNA
<213> ORGANISM: Bos taurus

<400> SEQUENCE: 198
gttactctaa catgggtggg attacaggtg atgctyggcc tcttcctccc cccaggtatt      60
tttagtggtc t                                                           71

<210> SEQ ID NO 199
<211> LENGTH: 71
<212> TYPE: DNA
<213> ORGANISM: Bos taurus

<400> SEQUENCE: 199
ctgaggccca gaggtgatct atgggcccta atggaygatg cagtccttgg ggaaggggat      60
ggacgagtgg t                                                           71

<210> SEQ ID NO 200
<211> LENGTH: 71
<212> TYPE: DNA

<213> ORGANISM: Bos taurus

<400> SEQUENCE: 200
ttgccgtcac aggctgcgtg gcctcatctg aggccyctgt ctcaccgttt cagtttccca    60
tttctttaac a    71

<210> SEQ ID NO 201
<211> LENGTH: 71
<212> TYPE: DNA
<213> ORGANISM: Bos taurus

<400> SEQUENCE: 201
acagcatctg gaattccttg agtggcagtg cagccragct cggactctga ggccagactc    60
cggggttcaa g    71

<210> SEQ ID NO 202
<211> LENGTH: 71
<212> TYPE: DNA
<213> ORGANISM: Bos taurus

<400> SEQUENCE: 202
tctctggatt tccagcaccc tagactgttg ccaaamttgg ctcccatgtg cctgggagga    60
ggtgcgggct g    71

<210> SEQ ID NO 203
<211> LENGTH: 71
<212> TYPE: DNA
<213> ORGANISM: Bos taurus

<400> SEQUENCE: 203
acagaaagat tttaaaaggc cagcaatact gttctktaat tcaacatcag ctcacgagct    60
tttctcatgt g    71

<210> SEQ ID NO 204
<211> LENGTH: 71
<212> TYPE: DNA
<213> ORGANISM: Bos taurus

<400> SEQUENCE: 204
cactgatccc aggaaccagc agccagacac caagakgtga cacactctat ggctcatgag    60
aatagaataa c    71

<210> SEQ ID NO 205
<211> LENGTH: 71
<212> TYPE: DNA
<213> ORGANISM: Bos taurus

<400> SEQUENCE: 205
atcccactga acagatgttt gtttcctgcc atggtyagtc atggcaaaag aaatgctaat    60
cttctgctat t    71

<210> SEQ ID NO 206
<211> LENGTH: 71
<212> TYPE: DNA
<213> ORGANISM: Bos taurus

<400> SEQUENCE: 206
tcccccagga acacttatat catgagtccc caagcmaaga gggccttccc agctcctcta    60
acatggatca c    71

<210> SEQ ID NO 207
<211> LENGTH: 71
<212> TYPE: DNA
<213> ORGANISM: Bos taurus

<400> SEQUENCE: 207
aggactcatc agccctgacc cttacctact gtcatyctca atcttaggcc cttctcatat     60
ccatttgtcc t                                                         71

<210> SEQ ID NO 208
<211> LENGTH: 71
<212> TYPE: DNA
<213> ORGANISM: Bos taurus

<400> SEQUENCE: 208
ttttaaaggg atagcctaag gaaccccact tgaatycttg gaggagggca tggtttctgc     60
attgagcctg g                                                         71

<210> SEQ ID NO 209
<211> LENGTH: 71
<212> TYPE: DNA
<213> ORGANISM: Bos taurus

<400> SEQUENCE: 209
actttcagaa acccatgtaa aaaacgatta taagcyctga acacaatgaa tgtatctggg     60
actcctgagg g                                                         71

<210> SEQ ID NO 210
<211> LENGTH: 71
<212> TYPE: DNA
<213> ORGANISM: Bos taurus

<400> SEQUENCE: 210
gtgcatcacc aggccaggat ccctggtcca aagctwtaaa acaagctgga cactcttcct     60
cttctgagca c                                                         71

<210> SEQ ID NO 211
<211> LENGTH: 71
<212> TYPE: DNA
<213> ORGANISM: Bos taurus

<400> SEQUENCE: 211
ttttcttttt aaggtcttta ttgatcttgg atgatrtttg ggatccttgg gtgttaaaag     60
cttttgacaa t                                                         71

<210> SEQ ID NO 212
<211> LENGTH: 71
<212> TYPE: DNA
<213> ORGANISM: Bos taurus

<400> SEQUENCE: 212
agacattttt ctaagaaaga tatagtaagg cccacrggca tgggattaga tacttaacaa     60
cagtagtcat t                                                         71

<210> SEQ ID NO 213
<211> LENGTH: 71
<212> TYPE: DNA
<213> ORGANISM: Bos taurus

<400> SEQUENCE: 213
gcggagagtc atgatggcgt ctgtatgatc tccggrggta gcggcgtcgg agttcggcca    60
aagtgagcgg c    71

<210> SEQ ID NO 214
<211> LENGTH: 71
<212> TYPE: DNA
<213> ORGANISM: Bos taurus

<400> SEQUENCE: 214
gcctctgtga actggaaact tcagaggttt atcggyaagc taagctgcag gccaagcagg    60
aggtcgataa c    71

<210> SEQ ID NO 215
<211> LENGTH: 71
<212> TYPE: DNA
<213> ORGANISM: Bos taurus

<400> SEQUENCE: 215
gagacgtata gattcctggg tcctttgcat ctggayggtt tgaatggata aagcaccact    60
tgacaaataa g    71

<210> SEQ ID NO 216
<211> LENGTH: 71
<212> TYPE: DNA
<213> ORGANISM: Bos taurus

<400> SEQUENCE: 216
aagacgctcc aagaggtgct gcagtgctcc tggtgwgggt ggcagtgccg tcgtgtgccc    60
caggcctgtg a    71

<210> SEQ ID NO 217
<211> LENGTH: 71
<212> TYPE: DNA
<213> ORGANISM: Bos taurus

<400> SEQUENCE: 217
tactcagaat attggacata tgctacgtac tcattycaca cattctcagg taagaaccaa    60
aaagagcctc a    71

<210> SEQ ID NO 218
<211> LENGTH: 71
<212> TYPE: DNA
<213> ORGANISM: Bos taurus

<400> SEQUENCE: 218
gctgaccaag aacggcccca aagttctgga atttamttgc cgtttcggtg atccagagtg    60
ccaagtgagt a    71

<210> SEQ ID NO 219
<211> LENGTH: 71
<212> TYPE: DNA
<213> ORGANISM: Bos taurus

<400> SEQUENCE: 219
ttattagcgt cctttgaggg tgggctcttg tgtttmcagc atttcttaaa ttgtaacttg    60
gaaaagatct g    71

```
<210> SEQ ID NO 220
<211> LENGTH: 71
<212> TYPE: DNA
<213> ORGANISM: Bos taurus

<400> SEQUENCE: 220
cgagtgtgaa tctataatat tacggtacaa cataaycttc aatattcata acagtactcc        60
taaagcagga a                                                              71
```